(12) United States Patent
Takishita et al.

(10) Patent No.: US 6,588,278 B1
(45) Date of Patent: Jul. 8, 2003

(54) ULTRASONIC INSPECTION DEVICE AND ULTRASONIC PROBE

(75) Inventors: Yoshihiko Takishita, Ishioka (JP); Hiroshi Yamamoto, Ishioka (JP)

(73) Assignee: Hitachi Construction Machinery Co., Ltd., Tokyo (JP)

( * ) Notice: Subject to any disclaimer, the term of this patent is extended or adjusted under 35 U.S.C. 154(b) by 38 days.

(21) Appl. No.: 09/629,840

(22) Filed: Jul. 31, 2000

(30) Foreign Application Priority Data

| Jul. 30, 1999 | (JP) | 11-217905 |
| Jul. 30, 1999 | (JP) | 11-217906 |
| Jul. 30, 1999 | (JP) | 11-217927 |
| Apr. 10, 2000 | (JP) | 2000-108423 |

(51) Int. Cl.[7] ............................................. G01N 29/04
(52) U.S. Cl. ........................ 73/618; 73/609; 73/620; 73/629
(58) Field of Search .................... 73/618, 622, 633, 73/640, 623, 644, 599, 600, 602, 627, 606, 607, 608, 609, 620, 629

(56) References Cited

U.S. PATENT DOCUMENTS

| 4,420,979 A | * | 12/1983 | Momii et al. ................. 73/644 |
| 4,537,073 A | * | 8/1985 | Ooshiro et al. ................ 73/602 |
| 4,574,637 A | * | 3/1986 | Adler et al. ................... 73/629 |
| 4,655,083 A | * | 4/1987 | Chubachi ..................... 73/606 |
| 4,674,334 A | * | 6/1987 | Chimenti et al. .............. 73/627 |
| 4,779,241 A | * | 10/1988 | Atalar et al. ................. 367/104 |
| 5,211,059 A | * | 5/1993 | Hayakawa et al. ............ 73/606 |
| 5,307,680 A | * | 5/1994 | Drescher-Krasicka ........ 73/606 |
| 5,433,113 A | * | 7/1995 | Andoh et al. .................. 73/622 |
| 5,974,889 A | * | 11/1999 | Trantow ....................... 73/624 |
| 6,070,468 A | * | 6/2000 | Degertekin et al. ........... 73/644 |
| 6,341,525 B1 | * | 1/2002 | Takada et al. ................ 73/627 |

\* cited by examiner

*Primary Examiner*—Helen Kwok
*Assistant Examiner*—Jacques Saint-Surin
(74) *Attorney, Agent, or Firm*—Crowell & Moring LLP

(57) ABSTRACT

An ultrasonic inspection device is constructed of an ultrasonic scanning unit, drive unit for the ultrasonic scanning unit, and a computing unit. The ultrasonic scanning unit is provided with an ultrasonic probe for two-dimensionally scanning a surface of a specimen with an ultrasonic wave through a medium such as water for the ultrasonic wave. The computing unit controls the ultrasonic scanning unit via the drive unit and performs an inspection for any flaw in a film formed on a surface of abase material as the specimen. From the ultrasonic probe to the specimen, an angled incident wave is transmitted such that a leaked elastic surface wave is induced, and a leaked wave from the specimen is received at the ultrasonic probe. When the adhesion is good, the reception level of the leaked wave becomes low. When the adhesion is poor, on the other hand, the reception level of the leaked wave becomes high. The computing unit evaluates the degree of adhesion of a spray deposit to the base material from the reception level of the leaked wave.

21 Claims, 37 Drawing Sheets

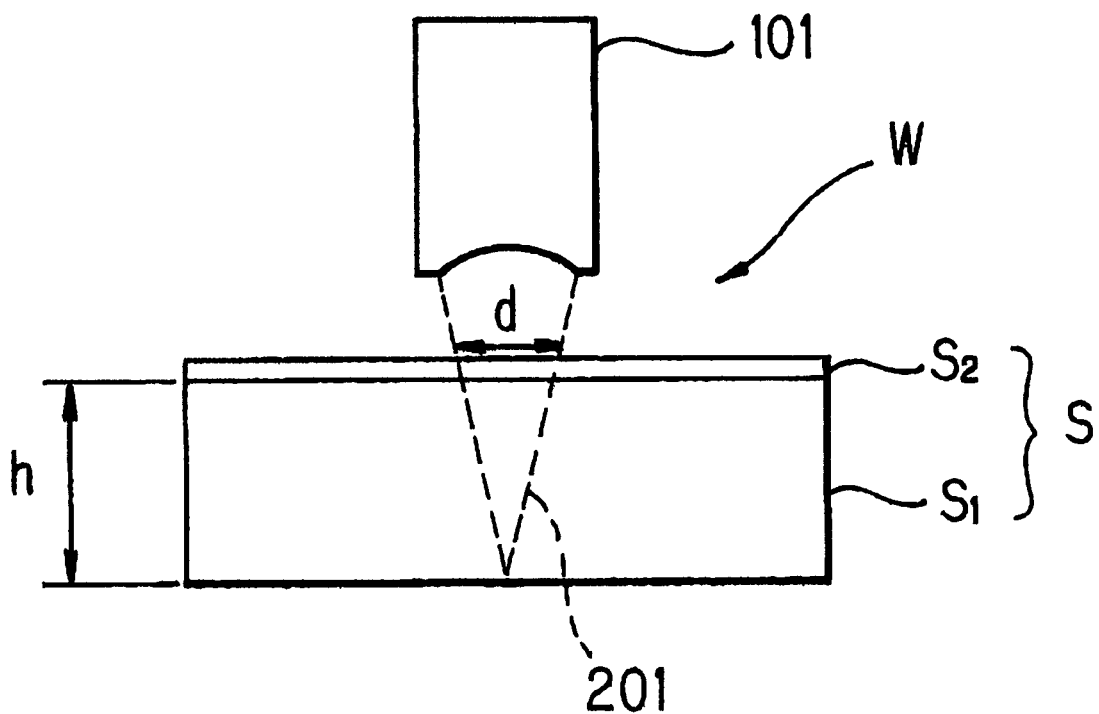

2mm

2mm

ULTRASONIC INSPECTION DEVICE AND ULTRASONIC PROBE

BACKGROUND OF THE INVENTION

1. a) Field of the Invention

This invention relates to an ultrasonic inspection device useful for the nondestructive inspection of a metallic material, for example, an ultrasonic inspection device suitable especially for the evaluation of soundness of a surface layer of a specimen. In addition, the present invention is also concerned with an ultrasonic probe useful for the nondestructive inspection of a specimen, especially with an ultrasonic probe suitable for the evaluation of soundness of a surface layer of a specimen and also for the detection of directionality of a flaw occurred in a specimen.

2. b) Description of the Related Art

As is described, for example, in JP 4-238265, it is conventionally known to nondestructively evaluate the adhesion of a spray deposit, which is formed on a surface of a metallic material, by using an ultrasonic wave.

To evaluate the adhesion of two materials at their interface, it has been a common practice to arrange a focused ultrasonic probe in opposition to the specimen, to bring the focal point of a supersonic wave, which has been transmitted from the ultrasonic probe, into registration with the interface between the two materials and then to detect the intensity of an echo from the interface. When the specimen is a spray deposit formed on a surface of a base material, however, the spray deposit is a thin film of 0.1 to 0.3 mm or so. Transmission of an ultrasonic wave to the specimen from the side of the spray deposit, therefore, practically does not make it possible to separate an echo from a surface of the spray deposit and an echo from an interface from each other, thereby failing to evaluate the adhesion of the spray deposit to the base material. Discussing, for example, about a 0.1-mm thick WC-based spray deposit formed on a surface of a base material, it is only an ultrasonic wave the frequency of which is within a range of from 5 to 20 MHz (200 to 50 ns in terms of period) that can be used for inspection because the spray melt causes a considerable high-frequency attenuation and has irregularities of from several micrometers to several tens micrometers or so on its surface. On the other hand, as the speed of a longitudinal wave through the spray deposit is about 4,200 m/s and the time difference between an echo from the surface of the spray deposit and an echo from the interface is only as small as 47.6 ns, it is understood that these echoes cannot be separated from each other.

Reference is now had to FIG. 1. In the spray deposit evaluation method described in the above-described conventional art, a specimen S with a spray deposit $S_2$ formed on a surface of a base material $S_1$ and a focused ultrasonic probe 101 are arranged in a face-to-face relationship in water (in the drawing, sign W indicates water as a medium for an ultrasonic wave), and a focal point of the ultrasonic probe 101 is brought into registration with a bottom surface of the base material $S_1$. From the intensity of a bottom echo, the adhesion of spray deposit $S_2$ to the base material $S_1$ is determined. According to this method, poor adhesion at the interface leads to more reflection of the ultrasonic wave at the interface, resulting in a decrease in the intensity of an echo from the bottom surface of the base material, while good adhesion at the interface allows an ultrasonic wave to transmit well through the base material $S_1$, resulting in an increase in the intensity of an echo from the bottom surface of the base material. Therefore, the adhesion of the base material and the spray deposit at their interface can be determined. It is also possible to ascertain an adhesion distribution of the spray deposit $S_2$ by two-dimensionally scanning a surface of the specimen S with the ultrasonic probe 101, inputting bottom echo levels at appropriate pitches and then displaying said bottom echo levels as an image on a C-scope.

According to the melt deposit evaluation method disclosed in the above-described conventional art, however, the ultrasonic wave 201 is transmitted to the specimen S from the side of the spray deposit $S_2$, and bottom echo levels of the base material $S_1$ are detected. Therefore, as is depicted in FIG. 2A, the irradiation diameter d of the ultrasonic beam on the surface of the spray deposit $S_2$ becomes greater and the detecting ability of a flaw drops, as the thickness h of the base material $S_1$ becomes greater.

For similar reasons as described above, the spray deposit evaluation method disclosed in the above-described conventional art leads to occurrence of a flaw inspection infeasible region at a relatively large region where, as shown in FIG. 2B, an end portion e of the specimen 100 is outside an irradiation range of the ultrasonic beam when two-dimensional scanning is performed along the surface of the specimen S by the ultrasonic probe 101. The end portion e of the specimen S is a location where a flaw tends to occur in the spray deposit $S_2$, and is especially important as a location to be inspected. Inclusion of such a large flaw inspection infeasible region is of a serious concern from the standpoint of increasing the reliability of a flaw inspection.

Further, the spray deposit evaluation method disclosed in the above-described conventional art is a method in which the adhesion between the base material $S_1$ and the spray deposit $S_2$ is indirectly evaluated from the levels of bottom echoes from the base material $S_1$. In addition to information indicative of the adhesion of the spray deposit $S_2$, the bottom echoes from the base material $S_1$, however, contain various information indicative of internal and bottom conditions of the base material $S_1$, for example, information on irregularities of the bottom surface and rust and the like deposited on the bottom surface and information on flaws inside the base material. Because these information and the information on the adhesion of the spray deposit $S_2$ cannot be separated from each other, the conventional spray deposit evaluation method is accompanied by a problem in that the evaluation of the spray deposit cannot be conducted precisely.

Moreover, for similar reasons as described above, the spray deposit evaluation method disclosed in the conventional art cannot obtain sufficient or complete bottom echoes and hence, cannot perform a practically sufficient inspection for a flow inside a spray deposit, when the base material $S_1$ comprises a material through which an ultrasonic wave undergoes a significant attenuation like nickel-based super alloys.

A description has been made above by taking, as an example, an inspection of a flaw in a spray deposit. It is however to be noted that similar inconveniences arise upon evaluating the soundness of a surface layer of a specimen in other characteristics and the like, such as existence/non-existence of a crack in the surface layer of the specimen, a stress distribution in the surface layer of the specimen, a fracture toughness value, thermal embrittlement or intergranular corrosion.

As is disclosed, for example, in JP 10-318995, a further technique is also known to nondestructively evaluate a stress distribution and a fracture toughness value of a specimen and also a deterioration of the specimen such as thermal embrittlement and intergranular corrosion (these properties will hereinafter be collectively called "deterioration or the like of a specimen") from variations in the speed of a leaked elastic surface wave which is one of ultrasonic modes.

FIG. 3A and FIG. 3B are a fragmentary cross-sectional view and a plan view, which illustrate one example of ultrasonic probes which have been conventionally used in this type of nondestructive inspections. As is readily appreciated from these drawings, an ultrasonic probe 101 has a construction that it is provided with a single-piece oscillator 102 formed in a disc shape in plan and an acoustic lens 103 in the form of a concave lens, said acoustic lens being for causing an ultrasonic wave, which has been transmitted from the oscillator 102, to converge and enter a specimen S. Around the oscillator 102, a damper material 101a is generally arranged to suppress generation of vibrations beyond necessity. The oscillator 102 is formed of a piezoelectric thin film with electrodes arranged on front and back sides thereof, respectively. On the other hand, the acoustic lens 103 is formed of a material having a high ultrasonic wave propagation speed such as aluminum, a setting surface 103a for the oscillator 102 is formed as a planar surface, and a lens curvature surface 103b which is located opposite the setting surface is formed as a spherical surface. The oscillator 102 is fixed with on the oscillator-setting surface 103 of the acoustic lens 103 by adhesion or the like.

Upon evaluating a deterioration or the like of the specimen, the ultrasonic probe 101 is fixedly mounted on a mechanical scanner (not show) which is movable in a three-dimensional direction, and is arranged in a face-to-face relationship with the specimen S in water. Its height position is adjusted such that, as is shown in FIG. 3A, a focal point P of the acoustic lens 103 is positioned somewhat below the surface of the specimen S. Sign $\Delta Z$ in the drawing indicates a defocus deviation of the focal point P from the surface of the specimen S. Assume that in this state, a drive voltage is supplied across the electrodes of the oscillator 102 from an unillustrated control unit. The oscillator 102 is then driven, and an ultrasonic wave transmitted from the oscillator 102 enters the specimen S through the acoustic lens 103 and water. Further, a reflection wave and a leaked wave from the specimen S travel through water and the acoustic lens 103 and are received at the oscillator 102.

Of the ultrasonic wave transmitted from the oscillator 102, an angled incident wave which has entered the surface of the specimen S at a Rayleigh critical angle $\theta_L$ after travelling along an angle path A→B→C is converted into a leaked elastic surface wave, which then advances along the surface of the specimen S. During propagation on and along the surface of the specimen S from a point C of incidence, this leaked elastic surface wave leaks at the Rayleigh critical angle $\theta_L$. The leaked wave which has leaked at a point D on the surface of the specimen then travels along a path D→E→F and is received at the oscillator 102. On the other hand, out of the ultrasonic waves transmitted from the oscillator 102, a vertical incident wave which has entered the surface of the specimen S after travelling along a path G→H→I is reflected back by the specimen S, and the resulting reflection wave (vertical reflection wave) then travels along a vertical path I→H→G and is received at the oscillator 102.

Between the timing of reception of the leaked wave and the timing of reception of the vertical reflection wave at the oscillator 102, there is a time difference based on a difference between distances, which the angled incident wave and leaked wave and the vertical incident wave and vertical reflection wave have traveled, respectively, after the transmission of the angled incident wave and vertical incident wave from the oscillator 102 until the leaked wave and vertical reflection wave are received at the oscillator 102. From this time difference $\Delta t$, a speed $V_W$ of an ultrasonic wave propagating through water which is interposed between the ultrasonic probe 101 and the specimen S and is a medium for the ultrasonic wave, and the defocus deviation of the acoustic lens 103, the speed $V_L$ of the leaked elastic surface wave can be calculated in accordance with the following formula, and from a change in the speed $V_L$ of the leaked elastic surface wave, a deterioration or the like of the specimen S can be evaluated.

$$V_L = V_W \{(\Delta t \cdot V_W / \Delta Z) - (\Delta t^2 \cdot V_W^2 / 4 \Delta Z^2)\}^{-\frac{1}{2}} \tag{1}$$

FIG. 4 depicts an echo waveform L of the leaked wave and echo waveform V of the vertical reflection wave, both received at the oscillator 102. The above-described time difference $\Delta t$ can be determined by measuring a peak-to-peak time difference between the echo waveform L of the leaked wave and the echo waveform V of the vertical reflection wave. Further, the speed $V_W$ of the ultrasonic wave propagating in water can also be determined by a measurement. In addition, the defocus deviation $\Delta Z$ of the acoustic lens 103 can be determined from the position of the surface of the specimen S, the setting position of the ultrasonic probe 101, and the focal distance of the acoustic lens 103

Incidentally, examples of a method for determining the speed $V_L$ of the leaked elastic surface wave can include, in addition to the above-mentioned method, a method which comprises using burst waves as incident waves from the oscillator 102, positively causing the resulting leaked wave and vertical reflection wave to interfere with each other, and then determining the speed of the leaked elastic surface from a dip cycle of a change curve (V(Z) curve) of the interference wave so formed. A description of this method is, however, omitted herein because it has no direct connection to the present invention.

Incidentally, to permit determination of the speed $V_L$ of the leaked elastic surface wave from the above-described formula (1) and to evaluate a deterioration or the like of the specimen S, it is necessary that as premises, the echo waveform L of the leaked wave and the echo waveform V of the vertical reflection wave can be clearly separated from the signals received at the oscillator 102 and their time difference $\Delta t$ can be measured. In general, an increase in the defocus deviation $\Delta Z$ of the acoustic lens 103 leads to an increase in the propagation distance of a leaked elastic surface wave and hence, to an increase in travelling distance between the path A→B→C→D→E→F and the path G→H→I→H→G. As is shown in FIG. 4, this makes it possible to separate the echo waveform L of the leaked wave and the echo waveform V of the vertical reflection wave from each other along the time axis and thus, to measure the time difference $\Delta t$. According to research by the present inventors, however, it has been found that, in the case of a specimen with a film through which a leaked elastic surface wave is susceptible to attenuation, for example, a spray deposit or the like applied on a surface of abase material, an echo waveform L of a Leaked wave and an echo waveform V of a vertical reflection wave cannot be clearly separated and the time difference $\Delta t$ cannot be measured, even when the defocus deviation $\Delta Z$ of the acoustic lens 103 was changed to various values. Described specifically, the present inventors conducted an experiment on a specimen with a spray deposit of a WC-based spray material applied to a thickness of 0.1 mm on a surface of a base material. When the defocus deviation ΔZ of the acoustic lens 103 was increased, attenuation of a leaked elastic surface wave became greater so that detection of an echo waveform L of a leaked wave became difficult. When the defocus deviation ΔZ of the acoustic lens 103 was decreased conversely, an echo waveform L of a leaked wave was buried in an echo waveform V of a vertical reflection wave, thereby making it difficult to separate those waveforms from each other and hence, failing to determine a time difference Δt.

A theoretical analysis will be made to the foregoing. When ultrasonic pulses of 10 MHz were transmitted to the specimen from an acoustic lens having a throat depth (length between points G and H in FIG. 3A) of 5 mm and made of aluminum (sound speed: 6,400 m/s) while setting the defocus deviation ΔZ at 0.2 mm, the propagation time of a vertical incident wave and a vertical reflection wave, which propagate along the path G→H→I→H→G shown in FIG. 3A, is 10.05 μs, because the speed $V_L$ of a leaked elastic surface wave propagating through the WC-based spray deposit is about 2,300 m/s (a value measured beforehand by using a spray deposit of the same type a surface of which had been polished) and the Rayleigh critical angle is about 41 degrees. On the other hand, the propagation time of an angled incident wave, a leaked elastic surface wave and a leaked wave, which propagate along the path A→B→C→D→E shown in FIG. 3A, is 10.1 μs. As the difference between these propagation times is 50 ns, that is, only a half of the cycle (100 ns) of the frequency used, the time difference Δt cannot be determined even if a weak leaked wave has already been received.

To evaluate a deterioration or the like of the specimen S by determining the speed $V_L$ of the leaked elastic surface wave in accordance with the above-described formula (1), the speed $V_W$ of the ultrasonic wave propagating through the water interposed between the ultrasonic probe 101 and the specimen S has to be specified. As is known well, however, the speed $V_W$ of an ultrasonic wave propagating in water varies depending on the water temperature, and within a temperature range employed in general, the speed of an ultrasonic wave varies by as much as several m/s per 1° C. temperature difference. To accurately determine the speed $V_L$ of the leaked elastic surface wave by the formula (1), it is therefore necessary to measure the water temperature whenever a test is conducted. A conventional ultrasonic inspection devices, therefore, required a temperature sensor for measuring a water temperature. This renders the construction complex, and requires irksome procedures that, whenever the speed $V_L$ of a leaked elastic surface wave is measured, the water temperature is measured to determine the speed of water. As a result, it becomes difficult to efficiently perform a measurement of the speed $V_L$ of the leaked elastic surface wave and hence, inspection of a deterioration or the like of a specimen.

The conventional art has been described by taking, as examples, stress distributions and fracture toughness values of specimens and deterioration of materials such as thermal embrittlement and intergranular corrosion. The conventional art also involves similar inconvenience when evaluating soundness of a surface of a specimen, such as existence or nonexistence of a crack in the surface of the specimen or existence or nonexistence of separation of a film arranged over the surface of the specimen.

As indicated by the formula (1), the prior art has been described by taking, as an example, the technique for evaluating a deterioration of a specimen from a change in the speed of a leaked elastic surface wave propagating through a surface layer of the specimen. The ultrasonic inspection method making use of a leaked elastic surface area, however, can also be applied as a method for evaluating soundness of a surface of a specimen, such as existence or nonexistence of a crack or existence or nonexistence of separation of a film, from a change in the level of a leaked wave leaked from the specimen.

Described specifically, a leaked elastic surface wave penetrates inside a specimen by 1 wavelength or so from a surface of the specimen. When the adhesion of a film to a base material is good, more of the leaked elastic surface wave which has penetrated inside the specimen penetrates the base material so that the level of a leaked wave received by an oscillator becomes lower. When the adhesion of a film to a base material is poor, on the other hand, an air layer is formed between the base material and the film due to their separation, and a leaked elastic surface wave is reflected at the interface between the air layer and the film. Accordingly, less of the leaked elastic surface wave penetrates the base material so that the level of a leaked wave received by the oscillator becomes higher. From the reception level of a leaked wave at the ultrasonic probe, it is therefore possible to determine at the computing unit whether the adhesion of the film to the base material is good or not.

When a flaw such as a crack exists in the surface layer of the specimen, on the other hand, the level of a leaked wave to be received by the oscillator becomes lower because the propagation of a leaked elastic surface wave in the surface layer of the specimen is prevented by the crack or the like. When the surface layer of the specimen does not contain a flaw such as a crack, on the other hand, the level of a leaked wave to be received by the oscillator becomes higher because the propagation of a leaked elastic surface wave in the surface layer of the specimen is not prevented by the crack or the like. Here again, from the reception level of the leaked wave at the ultrasonic probe, it is possible to determine at the computing unit whether or not a crack exists in the surface layer of the specimen.

For the evaluation of soundness of a surface layer of a specimen, use of an ultrasonic probe capable of detecting both a leaked wave and a vertical reflection wave is not absolutely necessary. It is, however, necessary to use an ultrasonic probe which can clearly detect an echo waveform of at least the leaked wave.

Further, the technique disclosed in JP 10-318995 referred to in the above can be applied as a method not only for evaluating a deterioration or the like of a specimen from a change in the speed of a leaked elastic surface wave propagating in a surface layer of the specimen but also for evaluating the soundness of the surface layer of the specimen, such as existence or nonexistence of a crack or existence or nonexistence of separation of a film, from a change in the level of a leaked wave leaking from the specimen.

As a technique for detecting directionality of a flaw developed in a specimen, on the other hand, it is known to detect a nonmetallic inclusion, which has occurred inside a rolled metal plate and extends in a rolling direction, by using a line-focus ultrasonic transmitter-receiver as disclosed, for example, in JP 11-51911. According to the technique disclosed in this patent publication, a flaw having directionality like a nonmetallic inclusion existing in a rolled metal plate can be detected with high accuracy, but neither evaluation of a deterioration of a specimen not evaluation of soundness of a surface layer of a specimen can be performed. This technique, therefore, cannot make the ultrasonic inspection of a specimen efficient. Further, the ultrasonic flaw detector according to the above-described conventional art uses the line-focus ultrasonic transmitter-receiver and, therefore, is accompanied by a problem that the detector becomes large and complex.

SUMMARY OF THE INVENTION

An object of the present invention is to provide an ultrasonic inspection device, which can evaluate soundness of a surface layer of a specimen with high accuracy irrespective of the thickness and bottom condition of a base material or the kind or the like of the material and moreover, to end portions of the specimen.

Another object of the present invention is to provide an ultrasonic inspection device which can calculate with high accuracy the speed of a leaked elastic surface wave without measuring the temperature of water, and also to provide an ultrasonic inspection device which can calculate with high accuracy the speed of a leaked elastic surface wave without measuring the temperature of water even in the case of a specimen in which the leaked elastic surface wave undergoes significant attenuation.

A further object of the present invention is to provide an ultrasonic probe useful in an ultrasonic inspection method that evaluates a deterioration or the like or soundness of a specimen by using a leaked elastic surface wave propagating in a surface layer of the specimen.

A still further object of the present invention is to provide an ultrasonic probe of a small and simple construction, which can detect directionality of a flaw existing in a surface layer, interior or bottom surface of a specimen.

According to the present invention, an ultrasonic scanning unit may be provided with an ultrasonic probe which performs transmission of an angled incident wave, which induces a leaked elastic surface wave, to a specimen and reception of a leaked wave from the specimen, and soundness of a surface layer of the specimen is evaluated from a level of the leaked wave received by the ultrasonic probe. The soundness of the surface layer of the specimen can, therefore, be evaluated with high accuracy irrespective of the thickness of the specimen, the bottom condition of the specimen or the internal condition or the like of the specimen and moreover, to end portions of the specimen.

According to the present invention, the speed of the leaked elastic surface wave may be calculated based on a difference between a propagation time of an angled incident wave, a leaked elastic surface wave and a leaked wave as measured with a focal point of the ultrasonic probe being registered with the surface of the specimen and a propagation time of an angled incident wave, a leaked elastic surface wave and a leaked wave as measured with the focal point of the ultrasonic probe being set in the specimen and also on a difference between a propagation time of a vertical incident wave and a vertical reflection wave as measured with the focal point of the ultrasonic probe being registered with the surface of the specimen and a propagation time of a vertical incident wave and a vertical reflection wave as measured with the focal point of the ultrasonic probe being set in the specimen. Measurement of the temperature of water is not necessary upon every inspection and a temperature sensor can be omitted. It is therefore possible to achieve simplification of the construction of the ultrasonic inspection device and also efficient computation.

In a focused ultrasonic probe provided with a flat ultrasonic probe, an oscillator-setting surface of which is formed as a planar surface, and an acoustic lens arranged on a free end portion of the flat ultrasonic probe and adapted to cause an ultrasonic wave, which has been transmitted from the oscillator, to converge, the present invention may use, as the acoustic lens, an acoustic lens constructed such that a propagation speed of an ultrasonic wave along propagation paths for a vertical incident wave to a specimen and a vertical reflection wave from the specimen and a propagation speed of an ultrasonic wave along propagation paths for an angled incident wave to the specimen and a leaked wave from the specimen differ from each other. It is therefore possible to shift the reception timing of a vertical reflection wave and the reception timing of a leaked wave, both by the oscillator, from each other, so that a difference $\Delta t$ in reception time between the resulting echo waveforms can be determined. Even in the case of a specimen with a film, in which the leakage elastic surface wave L is susceptible of attenuation, such as a spray deposit applied on a surface of a base material, its deterioration or the like can be nondestructively evaluated and moreover, the reception level of a leaked wave can be determined precisely. Therefore, the soundness of the surface of the specimen can also be evaluated nondestructively.

In a similar focused ultrasonic probe as described above, the present invention may use, as the acoustic lens, an acoustic lens which is provided with propagation paths for an angled incident wave to a specimen and a leaked wave from the specimen but is not provided with propagation paths for a vertical incident wave to the specimen and a vertical reflection wave from the specimen. The reception level of a leaked wave can therefore be determined precisely so that the soundness of a surface of the specimen can be evaluated.

According to the present invention, a concave lens a lens curvature surface of which is formed as a spherical surface may be used as an acoustic lens. An ultrasonic wave outputted from a flat ultrasonic probe can therefore be focused in the form or a spot on a surface layer of a specimen so that an high-accuracy inspection can be performed.

According to the present invention, a cylindrical lens may be used as an acoustic lens. An ultrasonic wave outputted from a flat ultrasonic probe can therefore be focused in the form of a line on a surface layer of a specimen so that an high-accuracy inspection can be performed with high efficiency.

According to the present invention, an acoustic lens may be detachably mounted on a free end portion of a flat ultrasonic probe. Focused ultrasonic probes of various specifications can therefore be obtained by combining the acoustic probe with various flat ultrasonic probes of different specifications. As a variety of ultrasonic inspections can be performed with fewer parts, the total cost of ultrasonic inspections can be reduced. The detachable connection between the flat ultrasonic probe and the acoustic lens permits assembly of a focused ultrasonic probe in water. This can avoid interposition of bubbles between the flat ultrasonic probe and the acoustic lens, thereby making it possible to provide inspection results with higher reliability. Because no labor is required for the elimination of bubbles, a reduction in inspection cost is also be possible here.

According to the present invention, an ultrasonic probe with an oscillator-setting surface formed as a spherical surface may be used instead of using the flat ultrasonic probe and the acoustic lens in combination, and at a central part on a surface of an oscillator arranged on the oscillator-setting surface, an ultrasonic shielding member smaller than the oscillator may be arranged. Simplification of the construction of the ultrasonic probe can hence be achieved.

In an acoustic lens, propagation paths for an angled incident wave to a specimen and a leaked wave from the specimen may be partly cut off. This makes it possible to impart directionality to the angled incident wave, which enters the specimen from an ultrasonic probe, and also to leaked wave, which enters the ultrasonic probe from the specimen, so that the S/N ratio of a detection signal of the leaked wave can be improved and the accuracy of detection of a line or plane defect can be heightened.

In a similar focused ultrasonic probe as described above, the present invention may use, as the acoustic lens, an acoustic lens which is provided with propagation paths for an angled incident wave to a specimen and a leaked wave from the specimen but is not provided with propagation paths for a vertical incident wave to the specimen and a vertical reflection wave from the specimen. The reception level of a leaked wave can therefore be determined precisely so that the soundness of a surface of the specimen can be evaluated.

In an ultrasonic inspection device provided with an ultrasonic scanning unit for, for example, two-dimensionally scanning a surface of a specimen with an ultrasonic wave through a medium such as water for the ultrasonic wave, a drive unit or the ultrasonic scanning unit, and a computing unit for controlling the ultrasonic scanning unit via the drive unit and performing a flaw detection of a surface layer of the specimen, the present invention features that the ultrasonic scanning unit is provided with an ultrasonic probe for performing transmission of an angled incident wave, which induces a leaked elastic surface wave, to the specimen and reception of a leaked wave from the specimen, whereby soundness of the surface layer of the specimen is evaluated at the computing unit from a level of the leaked wave received by the ultrasonic probe.

As is illustrated in FIG. 5A, among ultrasonic waves transmitted from an ultrasonic probe P1, an angled incident wave which has traveled along an angle path A→B→C and has entered at a Rayleigh critical angle $\theta_L$ a surface of a spray deposit $S_2$ is converted into a leaked elastic surface wave, and advances long the surface of the spray deposit $S_2$. This leaked elastic surface wave leaks at the Rayleigh critical angle $\theta_L$ while propagating on and along the surface of the spray deposit $S_2$. A leaked wave which has leaked at point D on the surface of the specimen travels along a path D→E→F and is received at an oscillator 2. Incidentally, the leaked elastic surface wave is said to penetrate the inside of the specimen S by a single wavelength or so from the surface of the specimen S (in the illustrated embodiment, the surface of the spray deposit $S_2$)

When the adhesion of the spray deposit $S_2$ to a base material $S_1$ is good, more of the leaked elastic surface wave which has penetrated inside the specimen S penetrates the base material $S_1$ so that the level of a leaked wave received by the oscillator 2 becomes lower. When the adhesion of the spray deposit $S_2$ to the base material $S_1$ is poor, on the other hand, an air layer is formed between the base material $S_1$ and the spray deposit $S_2$ due to their separation, and a leaked elastic surface wave is reflected at the interface between the air layer and the spray deposit $S_2$. Accordingly, less of the leaked elastic surface wave penetrates the base material $S_1$ so that the level of a leaked wave received by the oscillator 2 becomes higher. From the reception level of a leaked wave at the ultrasonic probe P1, it is therefore possible to determine at the computing unit whether the adhesion of the spray deposit $S_2$ to the base material $S_1$ is good or not.

When a flaw such as a crack exists in the surface layer of the specimen S which is not provided with a film such as a spray deposit, on the other hand, the level of a leaked wave to be received by the oscillator 2 becomes lower because the propagation of a leaked elastic surface wave in the surface layer of the specimen S is prevented by the crack or the like. When the surface layer of the specimen S does not contain a flaw such as a crack, on the other hand, the level of a leaked wave to be received by the oscillator 2 becomes higher because the propagation of a leaked elastic surface wave in the surface layer of the specimen S is not prevented by the crack or the like. Here again, from the reception level of the leaked wave at the ultrasonic probe 21, it is possible to determine at the computing unit the soundness of the specimen S. No particular limitation is imposed on the ultrasonic probe insofar as it can perform transmission of an angle incident wave, which induces a leaked elastic surface wave, to a specimen and reception of a leaked wave from the specimen.

To achieve the above-described objects, the present also features that, in an ultrasonic inspection device provided with an ultrasonic scanning unit, a drive unit for the ultrasonic scanning unit, and a computing unit for controlling the ultrasonic scanning unit via the drive unit and performing a desired ultrasonic inspection, said ultrasonic scanning unit having an ultrasonic probe and a mechanical scanner for moving the ultrasonic probe relative to a specimen, a speed of a leaked elastic surface wave is calculated at the computing unit based on a difference between a propagation time of an angled incident wave, the leaked elastic surface wave and a leaked wave when an ultrasonic wave is transmitted with a focal point of the ultrasonic probe being set at a first depth position in the specimen and a propagation time of an angled incident wave, a leaked elastic surface wave and a leaked wave when an ultrasonic wave is transmitted with the focal point of the ultrasonic probe being set at a second depth position in the specimen and also on a difference between a propagation time of a vertical incident wave and a vertical reflection wave when an ultrasonic wave is transmitted with the focal point of the ultrasonic probe being set at the first depth position in the specimen and a propagation time of a vertical incident wave and a vertical reflection wave when an ultrasonic wave is transmitted with the focal point of the ultrasonic probe being set at the second depth position in the specimen, a speed of the leaked elastic surface wave is calculated at the computing unit In the ultrasonic inspection device of the above-described construction, the first depth position can be set at the surface of the specimen while the second depth position can be set at a position such that a leaked elastic surface wave is produced on the specimen by an ultrasonic wave transmitted from the ultrasonic probe.

In the ultrasonic inspection device of the above-described construction, the first depth position can be set on the surface of the specimen, and the second depth position can be set at a position where a leaked elastic surface wave is produced in the specimen by an ultrasonic wave transmitted from the ultrasonic probe.

A time difference $\Delta t_L$ between a propagation time $t_{L0}$ of an ultrasonic wave along a path A→B→C→(D→) E→F when the position of the focal point of the acoustic lens 3 is brought into registration with the surface of the specimen S, for example, as illustrated in FIG. 23 to be described subsequently herein and a propagation time $t_{L1}$ of an ultrasonic wave along a path A→B→C→D→E→F when the position of the focal point of the acoustic lens 3 is shifted inwardly from the surface of the specimen S as depicted in FIG. 21A to be described subsequently herein can be represented by the following formula (2):

$$\Delta t_L = t_{L0} - t_{L1} = 2\{\{\Delta Z/\cos\theta_L \cdot V_W\} - \Delta Z \cdot \tan\theta_L/V_L\}\} \quad (2)$$

where $\Delta Z$: Defocus deviation of the acoustic lens 3
$\theta_L$: Rayleigh critical angle
$V_W$: Speed of sound in water
$V_L$: Speed of a leaked elastic surface wave Eliminating $\theta_L$ from the formula (2) by using $V_W = V_L \sin\theta_L$ in view of the Snell law of refraction, the following formula (3) can be obtained.

$$V_L = (1/V_W^2 - \Delta t_L^2/4\cdot\Delta Z^2)^{-\frac{1}{2}} \quad (3)$$

On the other hand, a time difference $\Delta t_V$ between a propagation time $t_{V0}$ of an ultrasonic wave along a path G→I→G when the position of the focal point of the acoustic lens 3 is brought into registration with the surface of the specimen S and a propagation time $t_{V1}$ of an ultrasonic wave along a path G→I→G when the position of the focal point of the acoustic lens 3 is shifted from the surface of the specimen S can be represented by the following formula (4):

$$\Delta t_V = t_{V0} - t_{V1} = 2\times\Delta Z/V_W \quad (4)$$

From this formula (4), the sound speed $V_W$ in water can be determined by the following formula (5):

$$V_W = 2\times\Delta Z/\Delta t_V \quad (5)$$

Here, introduction of the formula (5) into the formula (3) makes it possible to obtain the following formula (6) which determines the sound speed $V_L$ of a leaked elastic surface wave without including the sound speed $V_W$ of water as a variable:

$$V_L = 2\cdot\Delta Z\cdot(\Delta t_V^2 - \Delta t_L^2)^{-\frac{1}{2}} \quad (6)$$

Therefore, the speed of the leaked elastic surface wave can be calculated from the difference $\Delta t_L$ between the propagation time of the angled incident wave, the leaked elastic surface wave and the leaked wave as measured with the focal point of the ultrasonic probe being set on the surface of the specimen and a propagation time of the angled incident wave, the leaked elastic surface wave and the leaked wave as measured with the focal point of the ultrasonic probe being set inside the specimen, a difference $\Delta t_V$ between the propagation time of the vertical incident wave and the vertical reflection wave as measured with the focal point of the ultrasonic probe being set on the surface of the specimen S and the propagation time of the vertical incident wave and the vertical reflection wave as measured with the focal point of the ultrasonic probe being set inside the specimen S, and the defocus deviation $\Delta Z$ of the acoustic lens 3. It is therefore possible to achieve simplification of the construction of the ultrasonic inspection device and efficient computation.

Incidentally, usable examples of the ultrasonic probe can include an ultrasonic probe provided, as shown in FIG. 12A to be described subsequently herein, with a homogeneous acoustic lens 103 in which a propagation speed of an ultrasonic wave along the propagation paths (G→H and H→G) for a vertical incident wave and a vertical reflection wave and a propagation speed of an ultrasonic wave along the propagation paths (A→B and E→F) for an angled incident wave and a leaked wave are the same; and an ultrasonic probe provided, as shown in FIG. 21A, with an acoustic lens 3 in which a propagation speed of an ultrasonic wave along the propagation paths (G→I and I→G) for a vertical incident wave and a vertical reflection wave and a propagation speed of an ultrasonic wave along the propagation paths (A→B and E→F) for an angled incident wave and a leaked wave are different from each other.

The ultrasonic probe in FIG. 12A features small attenuation of a leaked elastic surface wave and permits separation of an echo waveform V of a vertical reflection wave and an echo waveform L of a leaked wave from each other along a time axis, and is applicable for the inspection of specimens each of which permits calculation of the time differences $\Delta t_L$ and $\Delta t_V$ in the formula (6). On the other hand, the ultrasonic probe in FIG. 21A can be applied not only for the inspection of specimens of the above-mentioned type but also for the inspection of specimens each of which, due to large attenuation of a leaked elastic surface wave, for example, as in the case of a specimen with a spray deposit formed thereon, does not permit separation of an echo waveform V of a vertical reflection wave and an echo waveform L of a leaked wave from each other along a time axis and does not permits calculation of the time differences $\Delta t_L$ and $\Delta t_V$ in the formula (6) when the below-described ultrasonic probe of FIG. 22 is used.

Incidentally, examples of a method for making a propagation speed of an ultrasonic wave along the propagation paths for a vertical incident wave and a vertical reflection wave in an acoustic lens and a propagation speed of an ultrasonic wave along the propagation paths for an angled incident wave and a leaked wave in the acoustic lens different from each other can include:

(a) to form a through-hole along the propagation paths for the vertical incident wave and the vertical reflection wave in the acoustic lens such that the through-hole extends from the setting surface for the oscillator to the lens curvature surface located opposite the setting surface;

(b) to form a recess in the lens curvature surface of the acoustic lens;

(c) to fill a filler, which is made of a material having a slower ultrasonic wave propagation speed than a material making up the acoustic lens, in a through-hole formed in the acoustic lens or in a recess formed in an oscillator-setting surface or lens curvature surface of the acoustic lens; and (d) to fill a filler, which is made of a material having a faster ultrasonic wave propagation speed than a material making up the acoustic lens, in a through-hole formed in the acoustic lens or in a recess formed in an oscillator-setting surface or lens curvature surface of the acoustic lens.

As a specific example of the above method (c), it can be mentioned to fill a resin in a through-hole or recess formed in an acoustic lens made of aluminum. As a specific example of the above method (d), on the other hand, it can be mentioned to press-fit a cylindrical body of aluminum in a through-hole or recess formed in an acoustic lens made of a resin or to perform out-sert molding of a resin around a core made of aluminum to form an acoustic lens.

No particular limitation is imposed on the shapes of the acoustic lens and oscillator. It is therefore possible to provide a concave lens, a curvature surface of which is formed as a spherical surface, with a single-piece oscillator formed in a disc shape in plan or to provide a cylindrical lens with a single or array-type oscillator.

When the propagation speed of an ultrasonic wave along the propagation paths for a vertical incident wave and a vertical reflection wave in an acoustic lens and the propagation speed of an ultrasonic wave along the propagation paths for an angled incident wave and a leaked wave in the acoustic lens are rendered different from each other, the timing of reception of the vertical reflection wave and the timing of reception of the leaked wave, both by the oscillator, can be shifted from each other even when the defocus deviation ΔZ cannot be increased due to significant attenuation of the leaked elastic surface wave. This makes it possible to clearly separate the echo waveform V of the vertical reflection wave and the echo waveform L of the leaked wave along the time axis, thereby permitting determination of the propagation times of the respective echoes. Accordingly, the speed $V_L$ of the leaked elastic surface wave can be easily determined by using the above-described formula (6). Even with respect to a specimen with a film, in which the leaked elastic surface wave is susceptible to attenuation like a spray deposit, applied on a surface of a base material, the above features make it possible to nondestructively evaluate the stress distribution and fracture toughness value of the specimen, the deterioration of the material such as thermal embrittlement and intergranular corrosion, and the soundness of the specimen such as the existence or nonexistence of a crack in the surface of the specimen and the existence or nonexistence of separation of the film arranged on the surface of the specimen.

In a focused ultrasonic probe provided with a flat ultrasonic probe, an oscillator-setting surface of which is formed as a planar surface, and an acoustic lens arranged on a free end portion of the flat ultrasonic probe and adapted to cause an ultrasonic wave, which has been transmitted from the oscillator, to converge, the present invention may feature use of an acoustic lens—which is constructed such that a propagation speed of an ultrasonic wave along propagation paths for a vertical incident wave to a specimen and a vertical reflection wave from the specimen and a propagation speed of an ultrasonic wave along propagation paths for an angled incident wave to the specimen and a leaked wave from the specimen differ from each other—as the acoustic lens.

Examples of the method for making a propagation speed of an ultrasonic wave along the propagation paths for a vertical incident wave and a vertical reflection wave in an acoustic lens and a propagation speed of an ultrasonic wave along the propagation paths for an angled incident wave and a leaked wave in the acoustic lens different from each other can include the above-mentioned methods (a) to (d).

When the propagation speed of an ultrasonic wave along the propagation paths for a vertical incident wave and a vertical reflection wave in an acoustic lens and the propagation speed of an ultrasonic wave along the propagation paths for an angled incident wave and a leaked wave in the acoustic lens are rendered different from each other, the timing of reception of the vertical reflection wave and the timing of reception of the leaked wave, both by the oscillator, can be shifted from each other even when the defocus deviation ΔZ cannot be increased. This makes it possible to clearly separate the echo waveform V of the vertical reflection wave and the echo waveform L of the leaked wave along the time axis, thereby permitting determination of the reception time difference Δt between the respective echoes. Therefore, the speed $V_L$ of the leaked elastic surface wave can be determined. Even with respect to a specimen applied with a film, in which the leaked elastic surface wave such as a spray deposit is susceptible to attenuation, applied on a surface of a base material, it is still possible to nondestructively evaluate its deterioration or the like. Further, the soundness of the surface layer of the specimen can also be evaluated nondestructively, because the echo waveform V of the vertical reflection wave and the echo waveform L of the leaked wave can be clearly separated from each other along the time axis and the reception level of the leaked wave can be determined precisely.

In a focused ultrasonic probe provided with a flat ultrasonic probe, an oscillator-setting surface of which is formed as a planar surface, and an acoustic lens arranged on a free end portion of the flat ultrasonic probe and adapted to cause an ultrasonic wave, which has been transmitted from the oscillator, to converge, the present invention may feature use of an acoustic lens—which is provided with propagation paths for an angled incident wave to a specimen and a leaked wave from the specimen but is not provided with propagation paths for a vertical incident wave to the specimen and a vertical reflection wave from the specimen—as the acoustic lens.

Examples of a method for eliminating the propagation paths for a vertical incident wave to the specimen and a vertical reflection wave from the specimen can include the following methods:

(e) to use, as the acoustic lens, an acoustic lens with a recess formed at a central part of an oscillator-facing side and to fill a space, which is formed by the oscillator-setting surface of the above-described flat ultrasonic probe and the recess, with air; and (f) to arrange an ultrasonic shielding member, which is smaller than the oscillator arranged on the flat ultrasonic probe, on the oscillator-facing side of the acoustic lens.

Use of an ultrasonic probe provided with an acoustic lens—which is provided with propagation paths for an angled incident wave to a specimen and a leaked wave from the specimen but is not provided with propagation paths for a vertical incident wave to the specimen and a vertical reflection wave from the specimen—as described above cannot obtain the echo waveform V of the vertical reflection wave and cannot determine the time difference Δt, but can still evaluate the soundness of the surface layer of the specimen because the reception level of the leaked wave can be determined precisely.

Incidentally, no particular limitation is imposed on the shape of the acoustic lens, A concave lens a curvature surface of which is formed as a spherical surface is usable, and a cylindrical lens is also usable.

When a concave lens is used, an ultrasonic wave can enter a specimen in the form of a spot so that a high-accuracy ultrasonic inspection can be performed. When a cylindrical lens is used, on the other hand, it is possible to have an ultrasonic wave enter a specimen in the form of a line, thereby making it possible to perform a high-accuracy ultrasonic inspection with high efficiency.

Incidentally, the acoustic lens can be integrally and inseparably fixed on a free end portion of a flat ultrasonic probe or as an alternative, can be detachably mounted on the free end portion of the flat ultrasonic probe.

Detachable mounting of the acoustic lens on the free end portion of the flat ultrasonic probe makes it possible to combine various flat ultrasonic probes of different specifications with the acoustic lens so that focused ultrasonic probes of various specifications can be obtained. Various ultrasonic inspections can therefore be conducted with a fewer number of parts, thereby making it possible to reduce the total cost of such ultrasonic inspections. Further, the detachable connection between the flat ultrasonic probe and the acoustic lens permits assembly of a focused ultrasonic probe in water. This can avoid interposition of bubbles between the flat ultrasonic probe and the acoustic lens, thereby providing inspection results with higher reliability. Because no labor is required for the elimination of bubbles, a reduction in inspection cost is also be possible here.

To achieve the above-described objects, the present invention may also provide a construction that in place of the construction making combined use of the flat ultrasonic probe and the acoustic lens, an ultrasonic probe an oscillator-setting surface of which is formed as a spherical surface is used and that an ultrasonic shielding member smaller than an oscillator is arranged at a central part on a surface of the oscillator arranged on the oscillator-setting surface.

Use of this ultrasonic probe is also unable to obtain an echo waveform V of a vertical reflection wave and to determine a time difference Δt, but can still evaluate the soundness of a surface layer of a specimen because the reception level of a leaked wave can be determined precisely.

In a focused ultrasonic probe provided with a flat ultrasonic probe, an oscillator-setting surface of which is formed as a planar surface, and an acoustic lens arranged on a free end portion of the flat ultrasonic probe and adapted to cause an ultrasonic wave, which has been transmitted from the oscillator, to converge, the present invention may also feature that the focused ultrasonic probe uses, as the acoustic lens, an acoustic lens constructed such that a propagation speed of an ultrasonic wave along propagation paths for a vertical incident wave to a specimen and a vertical reflection wave from the specimen and a propagation speed of an ultrasonic wave along propagation paths for an angled incident wave to the specimen and a leaked wave from the specimen differ from each other and that the propagation paths for the angled incident wave to the specimen and the leaked wave from the specimen are partly cut off.

Examples of a method for making a propagation speed of an ultrasonic wave along the propagation paths for a vertical incident wave and a vertical reflection wave in an acoustic lens and a propagation speed of an ultrasonic wave along the propagation paths for an angled incident wave and a leaked wave in the acoustic lens different from each other can include:

(g) to use, as the acoustic lens, an acoustic lens provided with a through-hole, which extends to a lens curvature surface, at a central part of an oscillator-facing side thereof and also with a slit narrower in width than a diameter of the through-hole and formed in the lens curvature surface;

(h) to use, as the acoustic lens, an acoustic lens provided with a through-hole, which extends to a lens curvature surface, at a central part of an oscillator-facing side thereof and also with a slit narrower in width than a diameter of the through-hole and formed in the lens curvature surface, and to fill fillers, which are made of a material having an ultrasonic wave propagation speed different from a material making up the acoustic lens, in the through-hole and slit;

(i) to use, as the acoustic lens, an acoustic lens provided with a recess, which is formed in a central part of a lens curvature surface, and also with a slit narrower in width than a diameter of the recess and formed in the lens curvature surface; and (j) to use, as the acoustic lens, an acoustic lens provided with a recess, which is formed in a central part of a lens curvature surface, and also with a slit narrower in width than a diameter of the recess and formed in the lens curvature surface, and to fill fillers, which are made of a material having an ultrasonic wave propagation speed different from a material making up the acoustic lens, in the recess and slit.

Usable examples of the fillers in the methods (h) and (i) can include those having a slower ultrasonic wave propagation speed than a material making up the acoustic lens and those having a faster ultrasonic wave propagation speed than a material making up the acoustic lens. Specific examples of the former example can include acoustic lens made of aluminum and having a through-hole or recess filled with a resin, while specific examples of the latter example can include acoustic lens made of a resin and having a through-hole or recess with a cylindrical body of aluminum press-fitted therein and an acoustic lens obtained by out-sert molding a resin around a core made of aluminum.

When the propagation speed of an ultrasonic wave along the propagation paths for a vertical incident wave and a vertical reflection wave in an acoustic lens and the propagation speed of an ultrasonic wave along the propagation paths for an angled incident wave and a leaked wave in the acoustic lens are rendered different from each other, a deterioration or the like of a specimen can be evaluated nondestructively as mentioned above even if the specimen is provided, on a surface of a base material, with a film, in which a leaked elastic surface wave is susceptible to attenuation, such as a spray deposit. Further, the echo waveform V of the vertical reflection wave and the echo waveform L of the leaked wave along the time axis can be clearly separated along the time axis, thereby permitting precise determination of the reception level of the leaked wave. The soundness of the surface layer of the specimen can therefore be evaluated nondestructively as mentioned above.

Propagation paths for an angled incident wave to a specimen and a leaked wave from the specimen may be partly cut off. This makes it possible to impart directionality to the angled incident wave, which enters the specimen from an ultrasonic probe, and also to the leaked wave, which enters the ultrasonic probe from the specimen, so that the S/N ratio (signal to noise ratio) of a detection signal of the leaked wave can be improved and the accuracy of detection of a line or plane defect can be heightened.

In a focused ultrasonic probe provided with a flat ultrasonic probe, an oscillator-setting surface of which is formed as a planar surface, and an acoustic lens arranged on a free end portion of the flat ultrasonic probe and adapted to cause an ultrasonic wave, which has been transmitted from the oscillator, to converge, the present invention may also feature that the focused ultrasonic probe uses, as the acoustic lens, an acoustic lens constructed such that the acoustic lens is provided with propagation paths for an angled incident wave to the specimen and a leaked wave from the specimen but is not provided with propagation paths for a vertical incident wave to the specimen and a vertical reflection wave from the specimen and the propagation paths for the angled incident wave to the specimen and the leaked wave from the specimen are partly cut off.

Examples of a method for eliminating the propagation paths for a vertical incident wave to the specimen and a vertical reflection wave from the specimen and partly cutting off the propagation path for an angle incident wave to the specimen and a leaked wave from the specimen can include the following methods:

(k) to use, as the acoustic lens, an acoustic lens with a recess formed at a central part of an oscillator-facing side and also with a slit, which is narrower in width than the diameter of the recess, formed in a radial direction of the oscillator-facing side, and further to fill a space, which is formed by the recess and slit and the flat ultrasonic probe, with air; and (l) to arrange an ultrasonic shielding member on the oscillator-facing side of the acoustic lens such that the ultrasonic shielding member covers the central part and radial parts of the oscillator.

Use of an ultrasonic probe provided with an acoustic lens—which is provided with propagation paths for an angled incident wave to a specimen and a leaked wave from the specimen but is not provided with propagation paths for a vertical incident wave to the specimen and a vertical reflection wave from the specimen—as described above cannot obtain the echo waveform V of the vertical reflection wave and cannot determine the time difference Δt, but can still evaluate the soundness of the surface layer of the specimen because the reception level of the leaked wave can be determined precisely.

When the propagation paths for an angled incident wave to a specimen and a leaked wave from the specimen are partly cut off in a similar manner as described above, directionality can be imparted to the angled incident wave, which enters the specimen from an ultrasonic probe, and also to the leaked wave, which enters the ultrasonic probe from the specimen, so that the S/N ratio of a detection signal of the leaked wave can be improved and the accuracy of detection of a line or plane defect can be heightened.

As each of the acoustic lenses of the above-described respective constructions, use of a concave lens the lens curvature surface of which is formed as a spherical surface is preferred because an ultrasonic wave can enter the specimen in the form of a spot and a high-accuracy ultrasonic inspection can be performed.

Further, in an ultrasonic probe provided with a flat ultrasonic probe, an oscillator-setting surface of which is formed as a planar surface, and an acoustic lens arranged on a free end portion of the flat ultrasonic, the present invention may feature use of an acoustic lens, an ultrasonic wave propagation path of which is partly cut off, as the acoustic lens.

Use of an ultrasonic probe provided with an acoustic lens, an ultrasonic wave propagation path of which is partly cut off as described above, can impart directionality to an ultrasonic wave, which enters the specimen from the ultrasonic probe, and also to an ultrasonic wave, which enters the ultrasonic probe from the specimen, so that the S/N ratio of echo signals can be improved and the accuracy of detection of a line or plane defect can be heightened.

Usable examples of a method for partly cut off the propagation path for the ultrasonic wave can include formation of a slit in the ultrasonic wave transmitting/receiving side of the acoustic lens.

Further, the ultrasonic wave transmitting/receiving side of the acoustic lens can be formed into a concave lens curvature surface or a flat surface. When the concave lens curvature surface is formed on the ultrasonic wave transmitting/receiving side, an ultrasonic wave transmitted from the oscillator can be focused in the form of a spot so that a high-accuracy ultrasonic inspection can be performed. When the ultrasonic wave transmitting/receiving side is formed into a flat surface, on the other hand, an ultrasonic wave transmitted from the oscillator can be caused to enter the specimen at once over a wide range of the specimen, so that a high-efficiency ultrasonic inspection can be performed.

In each of the above-described ultrasonic probes of the respective constructions, the acoustic lens can be integrally and inseparably fixed on the free end portion of the flat ultrasonic probe or can be detachably mounted on the free end portion of the flat ultrasonic probe. To detachably mount the acoustic lens on the flat ultrasonic probe, they can be detachably united together by cutting mutually-meshing threads beforehand in the acoustic lens and the flat ultrasonic probe and bringing them into threaded engagement. It is also possible to bring a self-tapping screw into threaded engagement with an internally-threaded bore, which is formed in a side wall of the acoustic lens, and to detachably fix the flat ultrasonic probe.

Detachable mounting of the acoustic lens on the free end portion of the flat ultrasonic probe makes it possible to combine various flat ultrasonic probes of different specifications with the acoustic lens so that focused ultrasonic probes of various specifications can be obtained. Various ultrasonic inspections can therefore be conducted with a fewer number of parts, thereby making it possible to reduce the total cost of such ultrasonic inspections. Further, the detachable connection between the flat ultrasonic probe and the acoustic lens permits assembly of a focused ultrasonic probe in water. This can avoid interposition of bubbles between the flat ultrasonic probe and the acoustic lens, thereby providing inspection results with higher reliability. Because no labor is required for the elimination of bubbles, a reduction in inspection cost is also be possible here.

BRIEF DESCRIPTION OF THE DRAWINGS

FIG. 1 is a schematic illustration showing a conventionally-known method for the ultrasonic inspection of a spray deposit;

DESCRIPTION OF THE PREFERRED EMBODIMENTS

1. First Embodiment 1.1 Overall Construction

Figure 6:
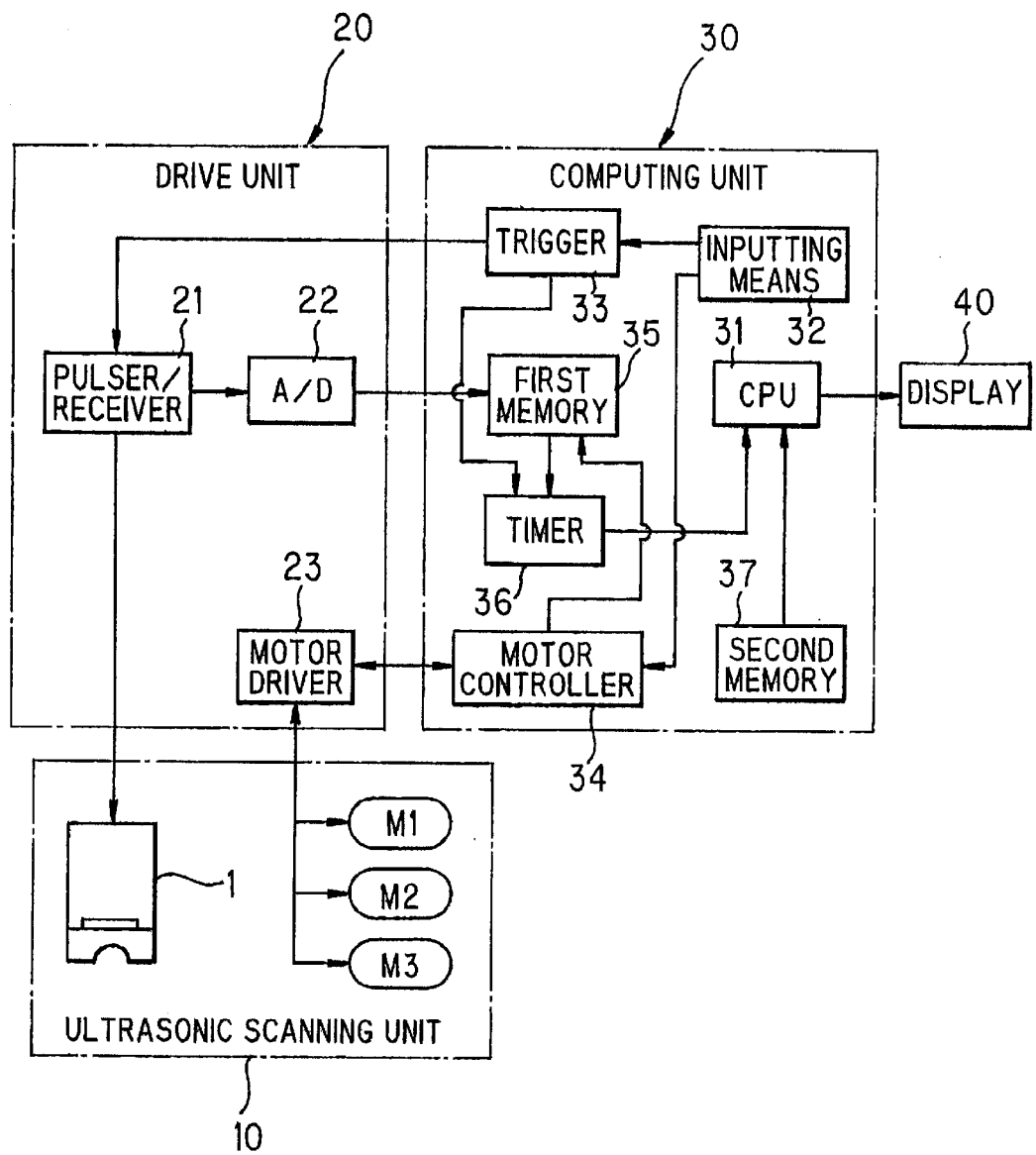
FIG. 6 is a block diagram illustrating the construction of an ultrasonic inspection device according to the first embodiment.

First, the overall construction of the ultrasonic inspection device according to the first embodiment of the present invention will be described with reference to FIG. 6 and FIG. 7.

As is illustrated in these drawings, the ultrasonic inspection device of this embodiment is constructed primarily of an ultrasonic scanning unit 10 for two-dimensionally scanning a surface of a specimen S with an ultrasonic wave along the surface of the specimen S, a drive unit 20 for the ultrasonic scanning unit 10, a computing unit 30 for converting reception levels of a leaked wave, which has been inputted at appropriate scanning pitches, into a C-scope image and determining the soundness of a surface layer of the specimen such as an adhesion distribution of a spray deposit $S_2$ and existence or nonexistence of a crack in the spray deposit $S_2$, and a display 40 for displaying the C-scope image as ultrasonic inspection results.

Figure 7:
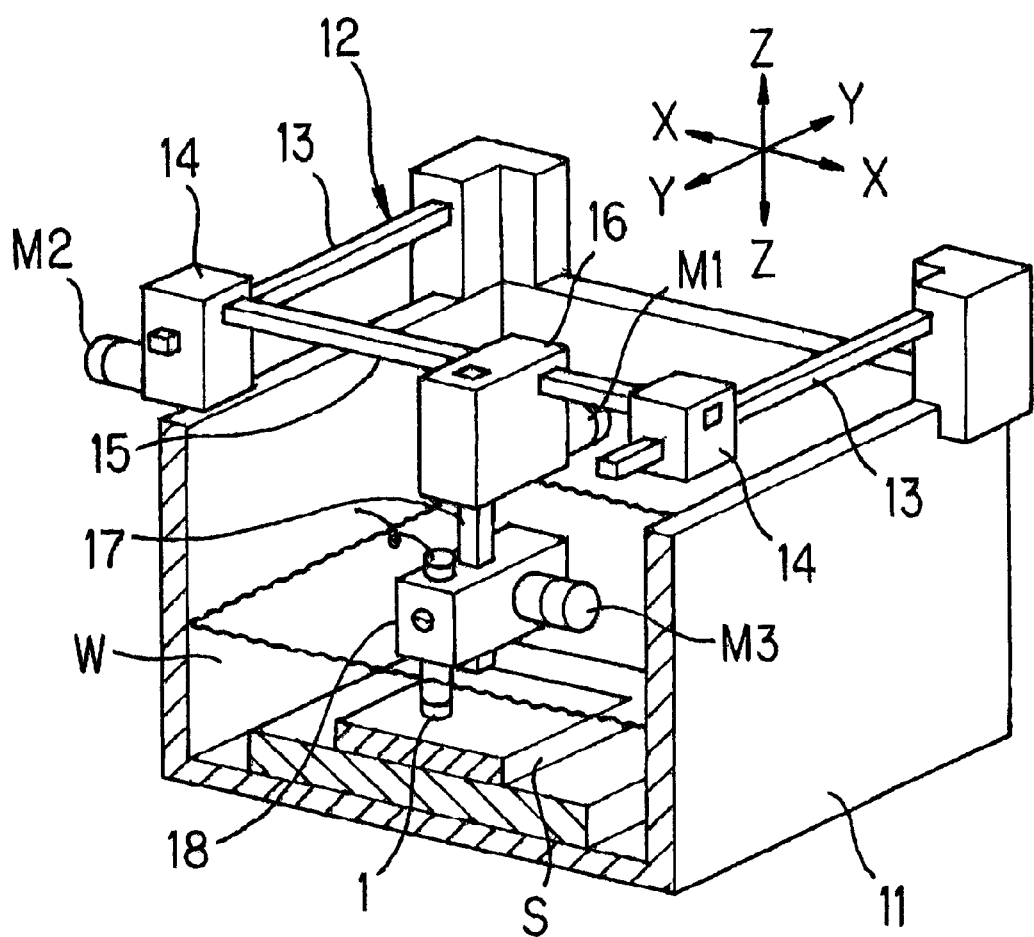
FIG. 7 is a perspective view showing the construction of an ultrasonic scanning unit in the ultrasonic inspection device according to the first embodiment.
Figure 8:
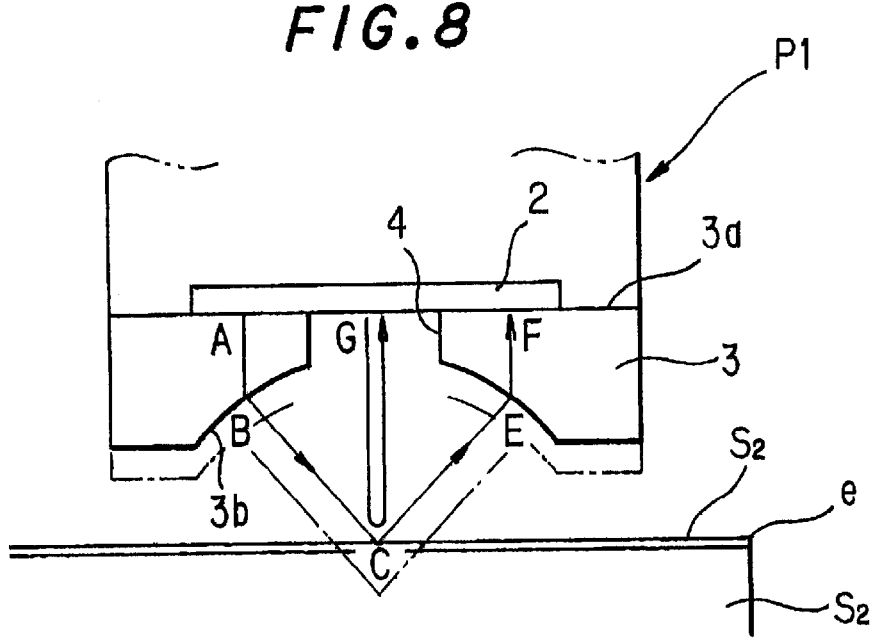
FIG. 8 is a schematic illustration showing a method for positioning the ultrasonic probe in direction Z in the first embodiment.

The ultrasonic scanning unit 10 comprises, as illustrated in FIG. 7, an ultrasonic probe 1, a water tank 11 for accommodating the ultrasonic probe 1 and the specimen S, said water tank 11 holding water W therein, and a mechanical scanner 12 for driving the ultrasonic probe 1 in three-dimensional direction. The mechanical scanner 12 has a pair of Y-axis guides 13 arranged in direction Y—Y along mutually-parallel two sides of the water tank 11, Y-axis sliders 14 for being guided direction Y—Y by the Y-axis guides 13, an X-axis guide 15 fixed at opposite ends thereof on the Y-axis sliders 14 and arranged in direction X—X, an X-axis slider 16 for being guided in direction X—X by the X-axis guide 15, an Z-axis guide 17 vertically fixed on the Z-axis slider 16, and a Z-axis slider 18 for being guided in direction Z—Z by the X-axis guide 17, said Z-axis slider 18 carrying the ultrasonic probe 1 thereon. The sliders 14, 16, 18 are driven by three motors M1–M3, respectively. These motors are individually provided with position signal outputting devices such as rotary encoders, so that coordinate data signals of the individual sliders 14, 16, 18 can be detected at the computing unit 30.

Usable as the ultrasonic probe 1 is an ultrasonic probe which can transmit an angled incident wave, which induces a leaked elastic surface wave, to the specimen S, can receive a leaked wave from the specimen S and can separate only an echo waveform of the leaked wave by an oscillator; or an ultrasonic probe of a construction such that an echo waveform of a leaked wave and an echo waveform of a vertical reflection waveform, both detected by the oscillator, can be separated along a time axis. Specific construction of the ultrasonic probe 1 will be described in detail subsequently herein.

The drive unit 20 is provided with a pulser/receiver 21 for performing transmission of an ultrasonic wave from the ultrasonic probe 1 and reception of an ultrasonic wave from the ultrasonic probe 1, an A/D converter 22 for converting signals, which have been received by the pulser/receiver 21, into digital signals, and a motor driver 23 for driving the three motors M1–M3 arranged on the mechanical scanner 12.

Further, the computing unit 30 is provided with a CPU 31, an inputting means 32 such as a keyboard or mouse, a trigger 33 for being driven by a command from the input means 32, a motor controller 34 for being actuated by a command from the input means 32 to control the motor 23, a first memory 35 for accumulating A/D converted reception signals along with coordinate data signals inputted from the motors M1–M3 via the motor driver 23 and the motor controller 34, a timer 36 for being actuated by a signal form the trigger 33 and setting a gate for signal processing by the CPU31, and a second memory 37 with procedures of signal processing by the CPU 31 stored therein.

1.2 Inspecting Method

One example of an ultrasonic inspection method making use of the ultrasonic inspection device constructed as described above will be described with reference to FIG. 6 through FIG. 9.

Figure 9:
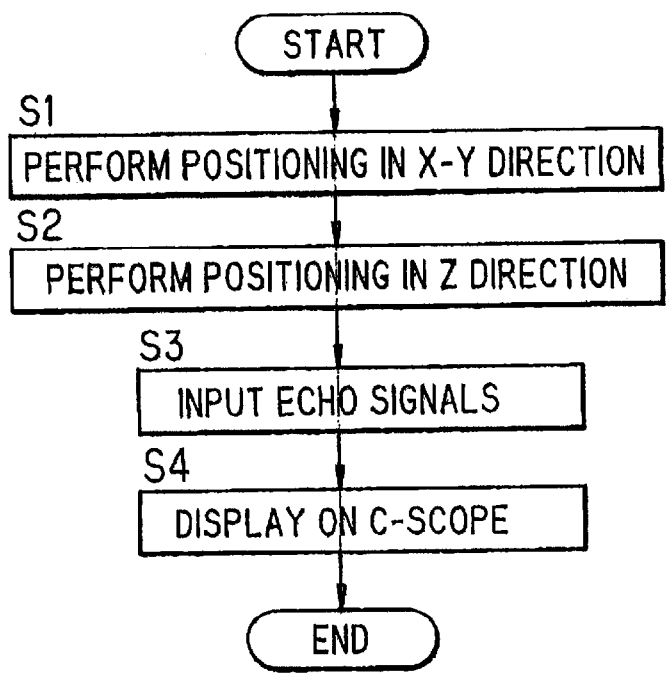
FIG. 9 is a flow chart illustrating processing procedures of an ultrasonic inspection method according to the first embodiment.

First in step S1 of FIG. 9, the inputting means 32 is operate to drive the motor M1, M2 mounted on the mechanical scanner 12, whereby positioning of the ultrasonic probe 1 is performed in direction X—Y relative to the specimen 5 set in the water tank 11. At this time, X—Y coordinate data of the ultrasonic probe 1 are inputted in the first memory 35 via the motor driver 23 and the motor controller 34, and the current position of the ultrasonic probe 1 is specified.

The routine then advances to step S2, in which the inputting means 32 is operated to drive the motor M3 mounted on the mechanical scanner 12 and hence to cause the ultrasonic probe 1, which is mounted on the Z-axis slider 18 of the mechanical scanner 12, to move in direction Z. As a consequence, the focal point of the acoustic lens 3 is caused to move downwardly by a desired defocus deviation $\Delta Z$ from the surface of the specimen S as indicated by a phantom in FIG. 8. Described specifically, the echo level of a leaked wave become maximum when the focal point of the acoustic lens 3 is brought into registration with the surface of the specimen S as indicated by sold lines in FIG. 8. By continuously monitoring the echo level of the leaked wave while causing the ultrasonic probe 1 to move in direction Z, the focal point of the acoustic lens 3 can be brought into registration with the surface of the specimen S. By causing the ultrasonic probe 1 to descend as much as the desired defocus deviation $\Delta Z$ from this position, the focal point of the acoustic lens 3 can be brought into registration with a predetermined position. This operation can be performed automatically based on a program which is stored in the second memory 37 arranged in the computing unit 30.

The greater the defocus deviation $\Delta Z$, the more the detection timing of a vertical reflection wave and the detection timing of a leaked wave are shifted from each other, thereby facilitating the detection of the level of the leaked wave. In contrast, the attenuation of a leaked elastic surface wave in the spray deposit $S_2$ becomes greater, leading to a drop in the level of the leaked wave. Taking both of them into parallel consideration, the defocus deviation $\Delta Z$ may preferably be set at 0.2 mm or so in the case of a spray melt of 0.1 mm in thickness.

The routine then advances to step S3. While two-dimensionally scanning in direction X—Y with the ultrasonic probe 1 in a desired range, an echo image of the leaked wave are inputted at desired scanning pitches together with coordinate data signals of the ultrasonic probe 1 in the first memory 35 arranged in the computing unit 30. This operation can also be performed automatically based on a program which is stored in the second memory 37 arranged in the computing unit 30.

The routine finally advances to step S4, in which the data accumulated in the first memory 35 are successively inputted in the CPU 31 to convert them into a C-scope image, and the results are displayed on the display 40. This operation can also be performed automatically based on a program which is stored in the second memory 37 arranged in the computing unit 30.

Figure 10A:
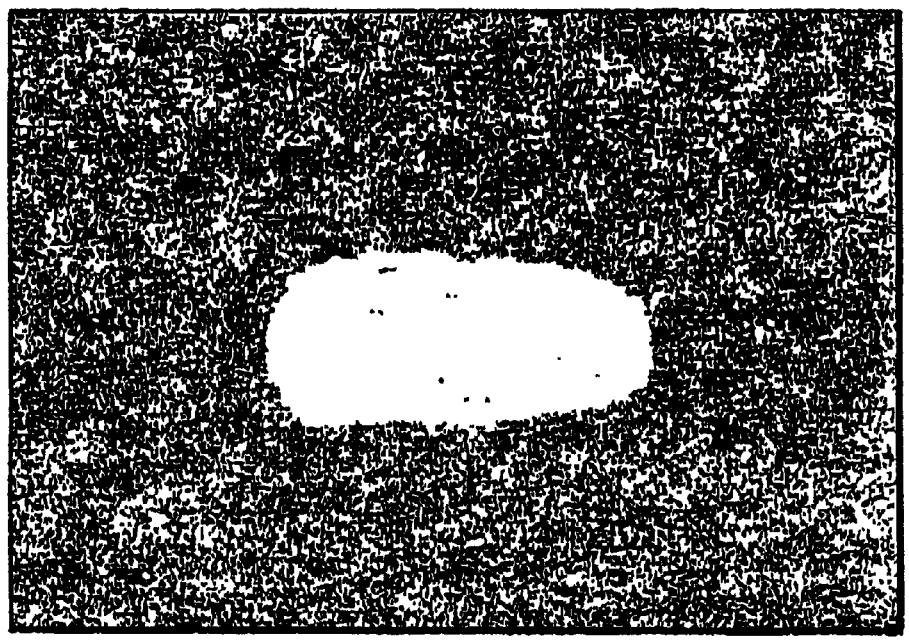
FIG. 10A and FIG. 10B are pictures showing C-image data of a leaked wave obtained by the ultrasonic inspection device according to the first embodiment.
Figure 10B:
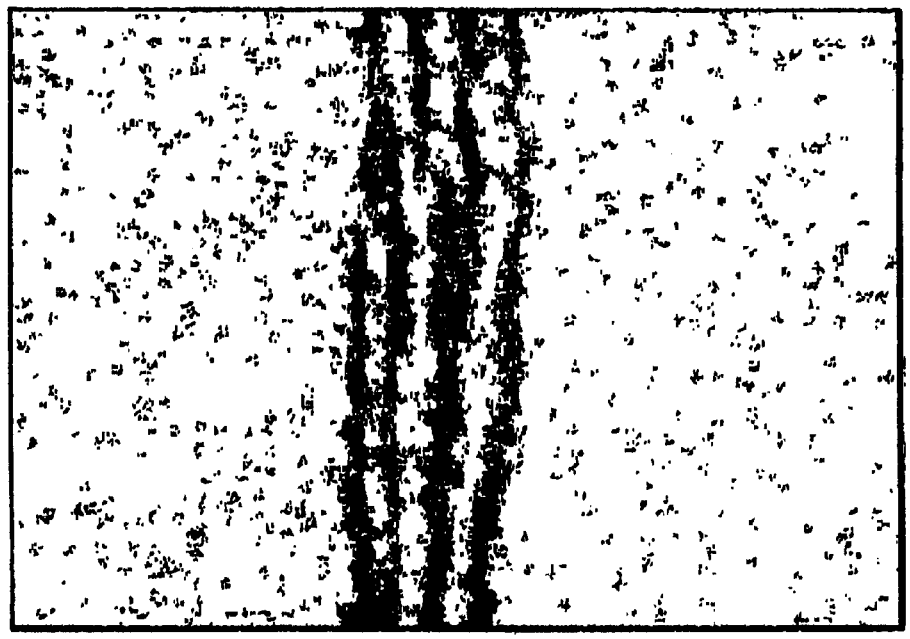

In FIG. 10A and FIG. 10B, C-scope images of leaked waves obtained by the device according to this embodiment are shown. FIG. 10A shows a C-scope image of a leaked wave, which was obtained from a specimen with a spray deposit $S_2$ formed without applying, only at a central part, blast cleaning, a pretreatment supposed to be applied to a base material $S_1$ before the formation of the spray deposit $S_2$. FIG. 10B shows a C-scope image of a leaked wave obtained from a specimen, which had a spray deposit $S_2$ normally formed on a surface of a base material $S_1$, after a bending stress had been applied subsequent to the formation of the spray deposit $S_2$.

In the case of FIG. 10A, the echo level of the leaked wave at the central part of the base material $S_1$, where no blast cleaning was applied, is evidently higher than that in the surrounding normal part. It is therefore understood that the device according to this embodiment can clearly show separation or insufficient adhesion of the spray deposit $S_2$ as an image. In the case of FIG. 10B, a stripe-shaped echo image where the echo level of a leaked wave is clearly lower than that in the surrounding normal part appeared at the central part of the base material $S_1$. It is hence understood that a very narrow crack (2 to 5 $\mu$m in width), which cannot be observed by naked eye, can be clearly shown as an image. In each of those cases, it was possible to perform the flaw inspection to an end portion e (see FIG. 8) of the specimen S.

Incidentally, when a similar inspection was conducted using, as the ultrasonic probe 1, one capable of performing transmission of an angled incident wave, which induces a leaked elastic surface wave, to the specimen S and reception of a leaked wave from the specimen S but incapable of separating an echo waveform of the leaked wave and an echo waveform of a vertical reflection wave, both detected by the oscillator, from each other along the time axis, a level difference in echo level between a normal part and a flaw part was so small that detection of a flaw was difficult.

1.3 Ultrasonic Probe

A description will hereinafter be made about examples of an ultrasonic probe to be arranged in the ultrasonic inspection device according to the present invention.

1.3.1 First Example of the Ultrasonic Probe

A first example of the ultrasonic probe to be arranged in the ultrasonic inspection device according to the present invention will be described with reference to FIG. 5A and FIG. 5B.

Figure 2A:
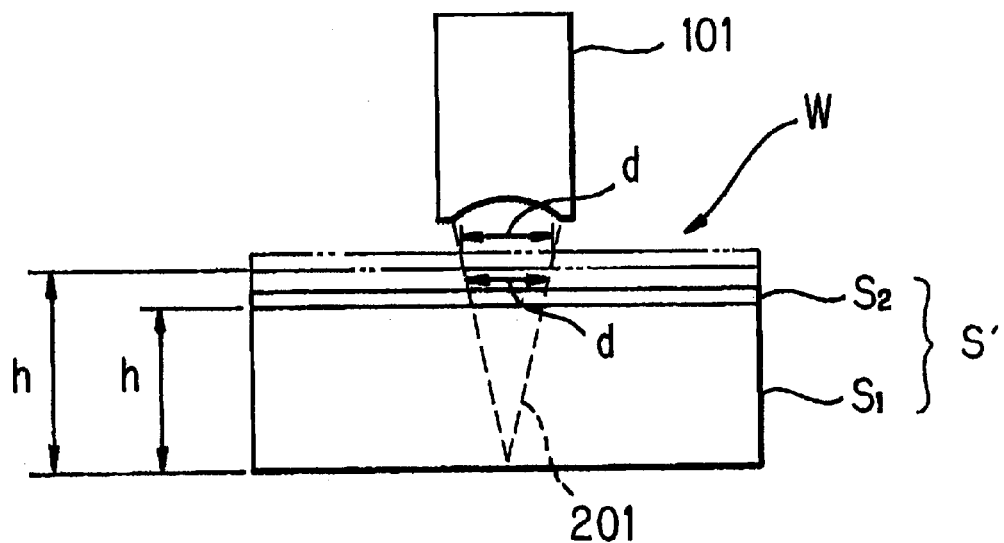
FIG. 2A and FIG. 2B are schematic illustrations showing a drawback of the conventional art.
Figure 2B:
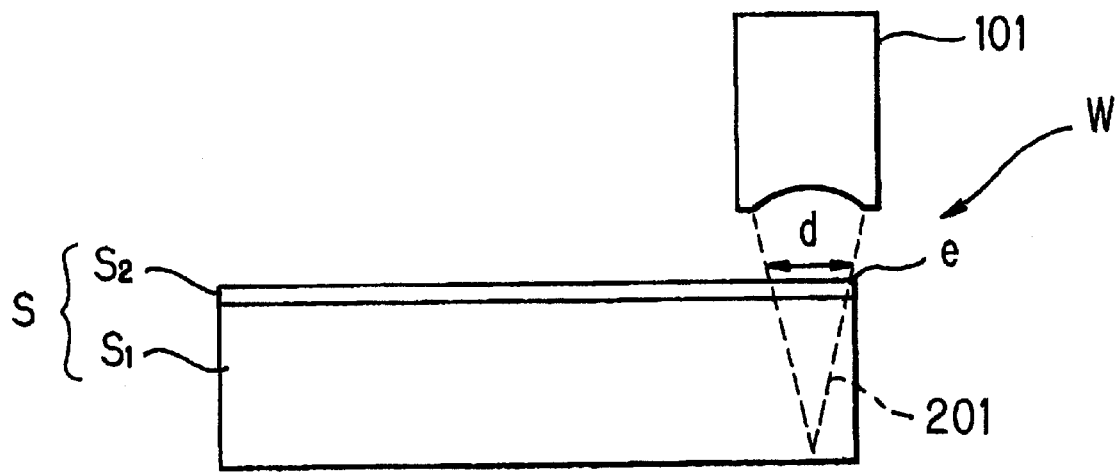
Figure 3A:
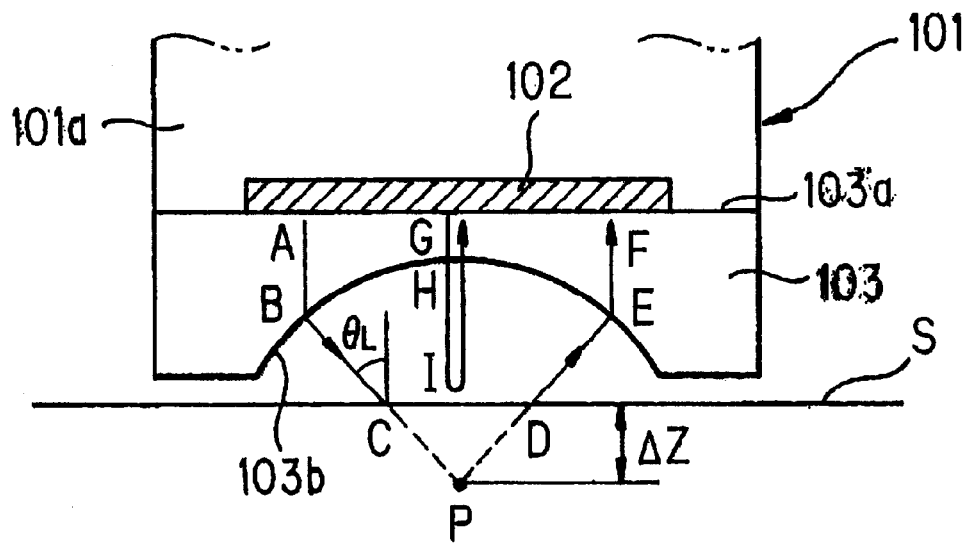
FIG. 3A and FIG. 3B are a fragmentary cross-sectional view and a plan view, which show an example of ultrasonic probes which have conventionally been used in nondestructive inspections of this kind.
Figure 3B:
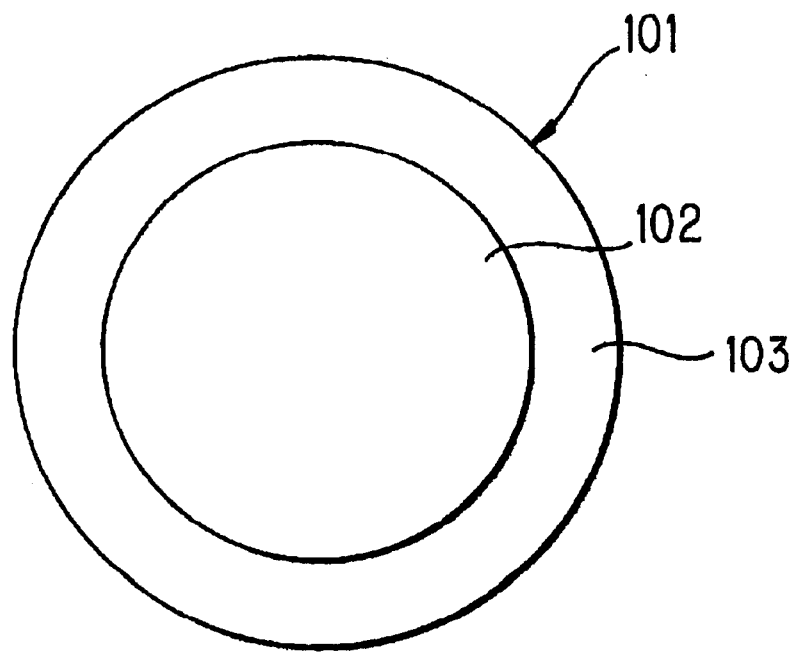
Figure 4:
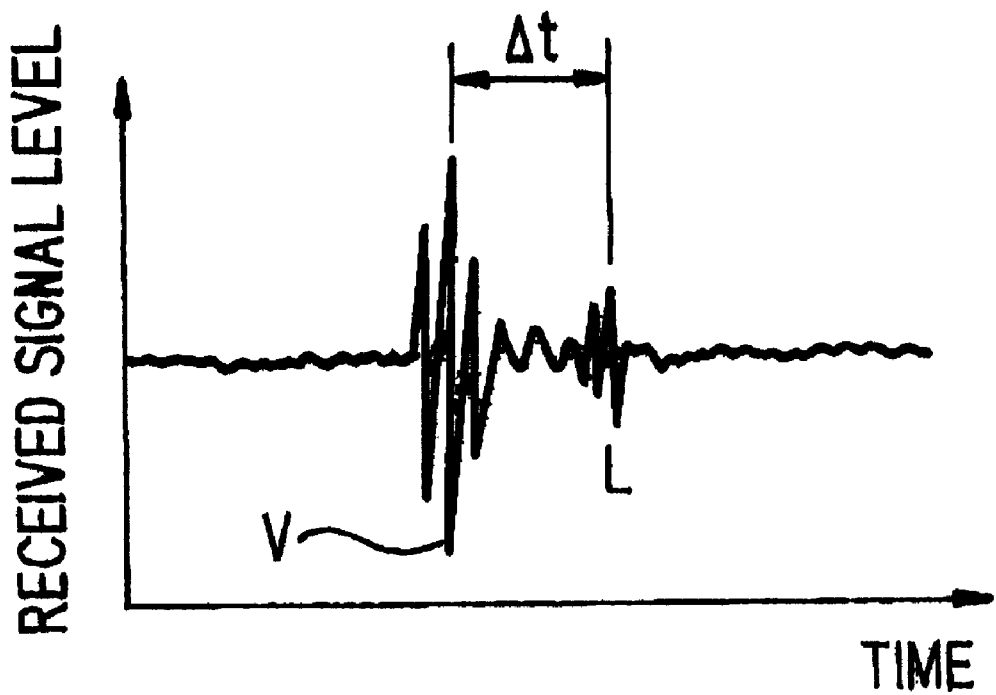
FIG. 4 is a diagram showing an echo waveform of a leaked wave and an echo waveform of a vertical reflection wave, which were both received by an oscillator.
Figure 5A:
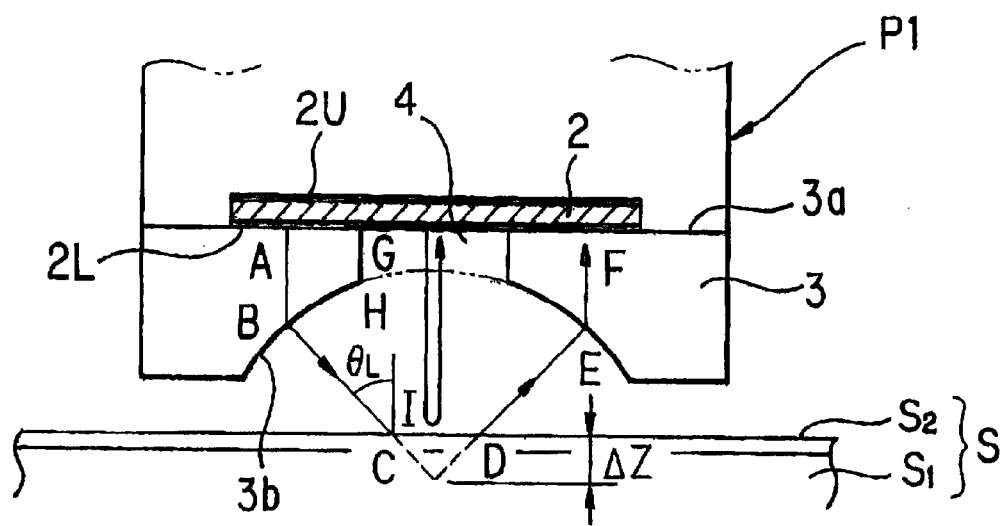
FIG. 5A and FIG. 5B are a fragmentary cross-sectional view and a plan view of a first example of an ultrasonic probe according to a principle and a first embodiment of the present invention.
Figure 5B:
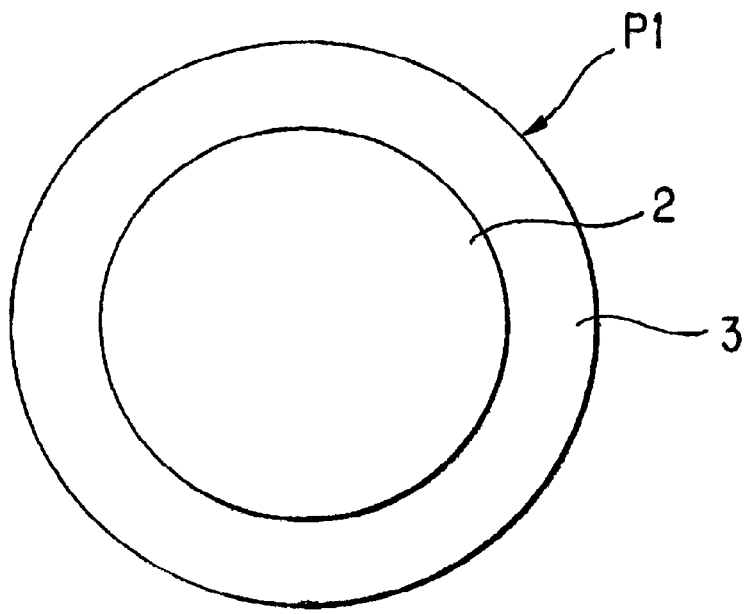

As is readily envisaged from FIG. 5A and FIG. 5B, an ultrasonic probe P1 of this example is provided with a single-piece oscillator 2, which is formed in a disc shape in plan, and also with an acoustic lens 3 of the concave lens type for causing an ultrasonic wave, which has been transmitted from the oscillator 2 to converge and enter the specimen S. At a central part of the acoustic lens 3, a through-hole 4 is formed extending from a planar side (setting surface), on which a transmitting and receiving surface of the oscillator 2 is mounted, to a lens curvature surface 3b. The oscillator 2 is formed of a piezoelectric thin film provided on upper and lower surfaces sides with an upper electrode 2U and a lower electrode 2L, respectively. On the other hand, the acoustic lens 3 is made of a material having a high ultrasonic wave propagation speed, such as aluminum, and its oscillator-facing side is formed as a planar surface while its lens curvature side is formed as a spherical surface.

On the side of the upper electrode 2U of the ultrasonic probe P1, a damper material may be arranged to suppress generation of vibrations beyond necessity. On the side of the lower electrode 2L, on the other hand, a protective plate may be arranged for the oscillator 2. Although the diameter of the through-hole 4 is sufficient when it is set equal to or greater than a propagation range of a vertical incident wave indicated by the path G→K→I and a vertical reflection wave indicated by the path I→H→G, it is preferred, from the standpoint of minimizing reception of noise, to make the diameter as great as possible within a range not interfering with propagation of an angled incident wave indicated by the path A→B→C and a leaked wave indicated by the path D→E→F.

Figure 11:
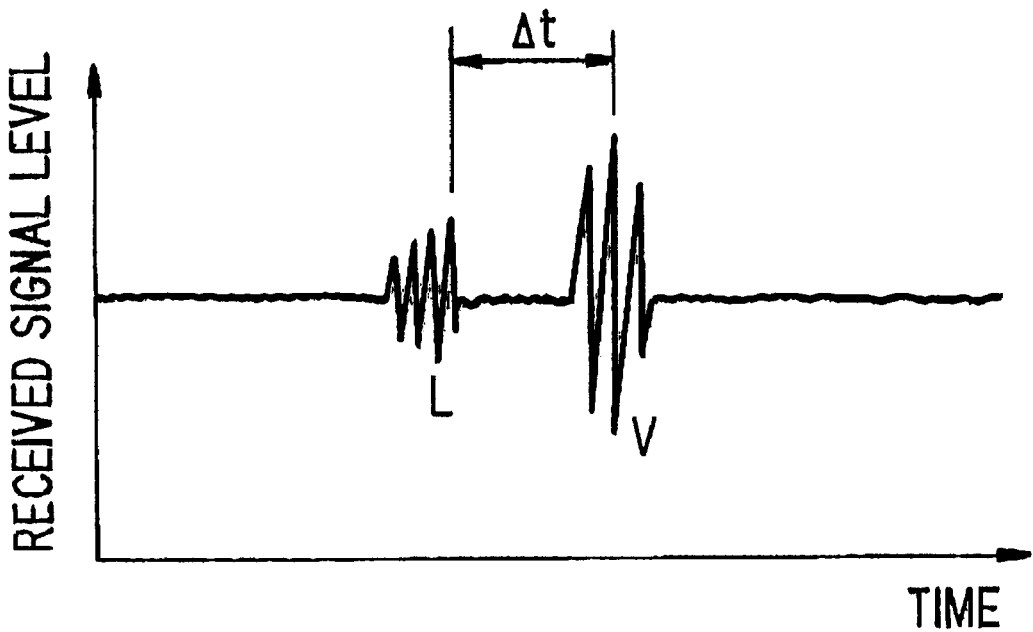
FIG. 11 is a diagram showing echo waveforms of a leaked wave and a vertical reflection wave, which were both received by an ultrasonic probe according to the first, second, third or fourth embodiment.

As has been described above, the ultrasonic probe is arranged together with the specimen S in water upon evaluation of the specimen S. When the ultrasonic probe 1A according to this embodiment in which the through-hole 4 is formed in the central part of the acoustic lens 3 is used, the aluminum-made acoustic lens 3 having a high ultrasonic wave propagation speed (sound speed: about 6,400 m/s) and water having a low ultrasonic wave propagation speed (about 1,480 m/s at 19° C., about 1,500 m/s at 26° C.) are interposed between the angle paths A→B→C and D→E→F of the oscillator 2 and the specimen S as illustrated in FIG. 5A. In contrast, it is only water having a low ultrasonic wave propagation speed that is interposed between vertical paths G→(H)→I and I→(H)→G of the oscillator 2 and the specimen S. Accordingly, the propagation time of the vertical incident wave and vertical reflection wave along the path G→(H)→I→(H)→G becomes longer than the propagation time of the angled incident wave, leaked elastic surface wave and leaked wave along the path A→B→C→D→E→F. As indicated by the echo waveform of the leaked wave and vertical reflection wave received by the oscillator in FIG. 11, reception signals are obtained in such a way that the echo waveform V of the vertical reflection wave and the echo waveform V of the leaked wave are separated from each other and the echo waveform L of the leaked wave appears ahead of the echo waveform V of the vertical reflection wave. From the echo waveform L of the leaked wave, its level (amplitude) can be determined accordingly. From its value, it is possible to determine whether the adhesion of the spray deposit $S_2$ to the base material $S_1$ is good or not or whether there is a crack or not.

A time difference between an echo waveform V of a vertical reflection wave and an echo waveform L of a leaked wave will now be determined, for example, by using a specimen with a 0.1-mm thick WC-based spray deposit applied to the surface of a base material and an acoustic lens having a lens throat thickness (length between points G and H in FIG. 5A) of 5 mm and made of aluminum (sound speed: 6,400 m/s) and by also assuming that the defocus deviation $\Delta Z$ is 0.2 mm, the frequency to be used is 10 MHz, the speed of a leaked elastic surface wave propagating in the WC-based spray deposit is 2,300 m/s (a value measured beforehand by using a spray deposit of the same type a surface of which had been polished) and the Rayleigh critical angle is 41 degrees. The propagation time of an ultrasonic wave propagating along the path G→(H)→I→(H)→G is about 15 µs as opposed to about 10 µs as the propagation time of an ultrasonic wave propagating along the path A→B→C→D→E→F. Their difference is hence 5 µs (50 times of the period of the frequency used). It is thus understood that both of the echo waveforms can be clearly separated along the time axis. Although the frequency to be used was assumed to be 10 MHz in the above example, similar results were also obtained when the frequency was varied within a range of from 5 to 20 MHz.

Figure 12A:
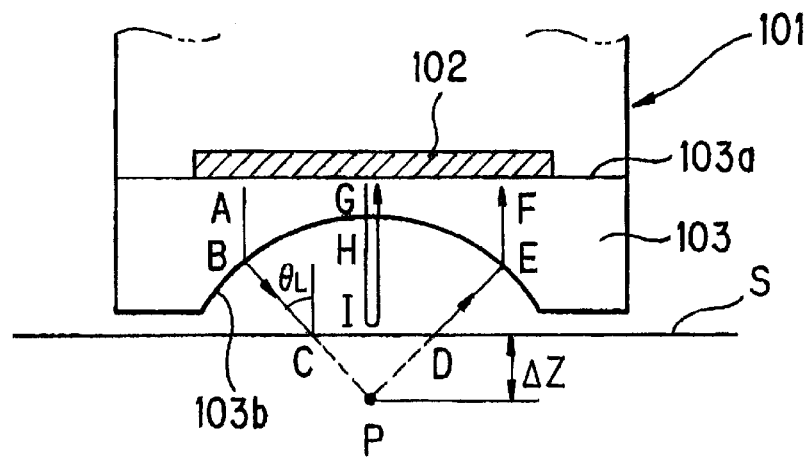
FIG. 12A and FIG. 12B are a fragmentary cross-sectional view and a plan view of an ultrasonic probe according to a comparative example to the first embodiment or a second example of the second embodiment.
Figure 12B:
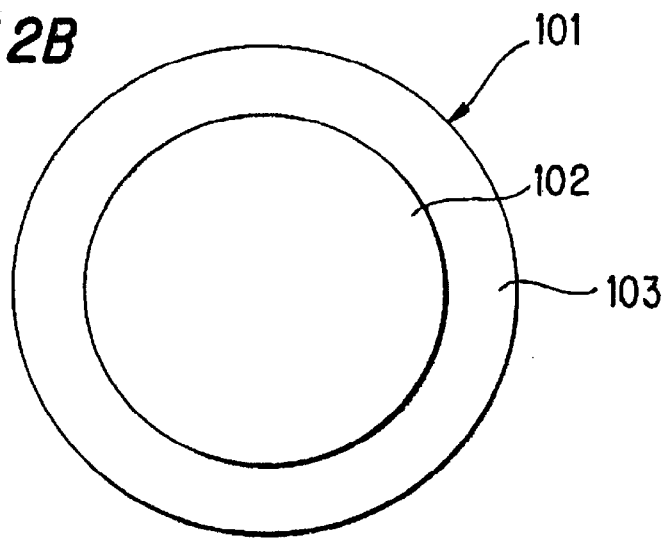
Figure 13:
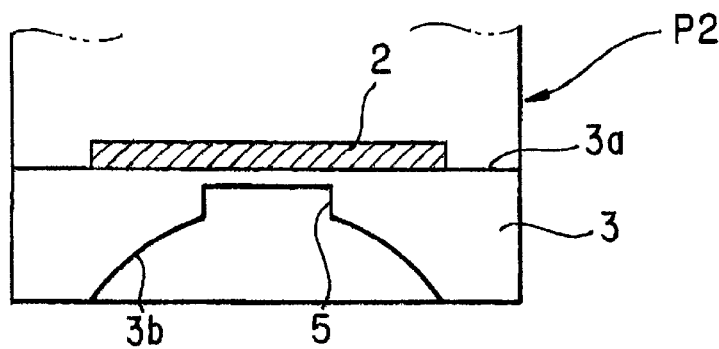
FIG. 13 is a fragmentary cross-sectional view of a second example of the ultrasonic probe according to the first embodiment or of an ultrasonic probe according to a third example of an eleventh embodiment.
Figure 14A:
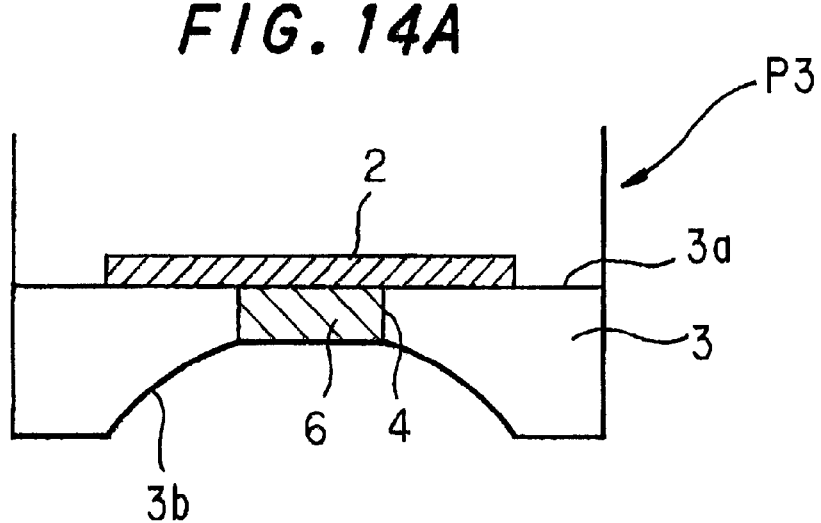
FIG. 14A, FIG. 14B and FIG. 14C are fragmentary cross-sectional views of an ultrasonic probe according to a third example of the ultrasonic probe according to the first embodiment.
Figure 14B:
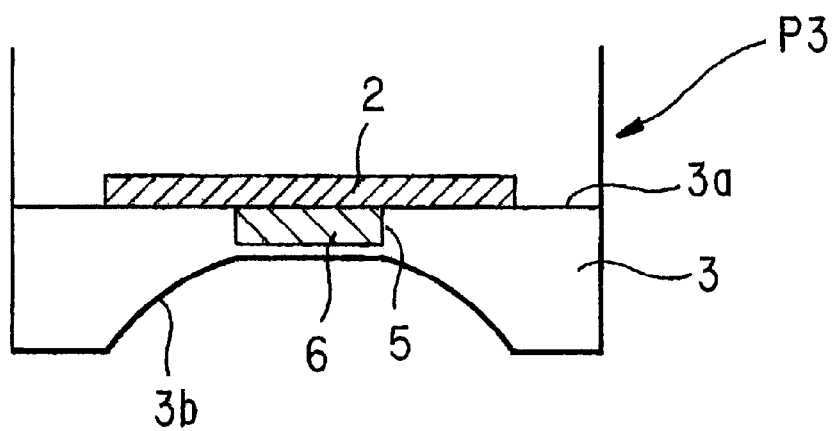
Figure 14C:
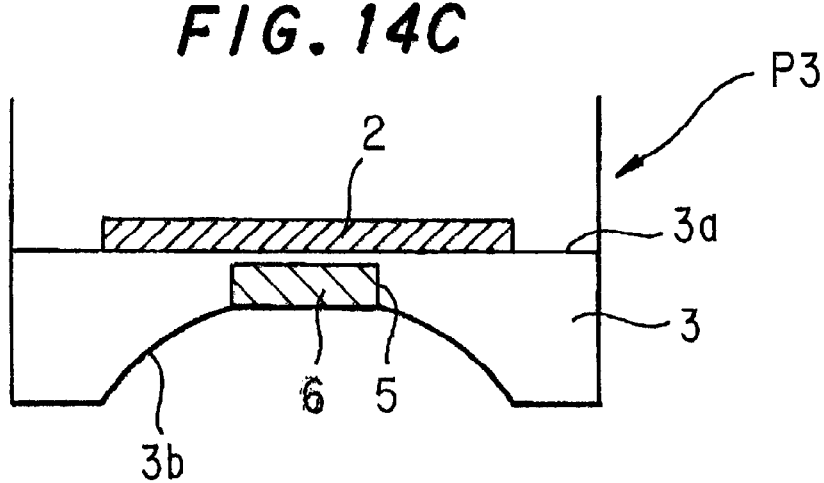
Figure 15A:
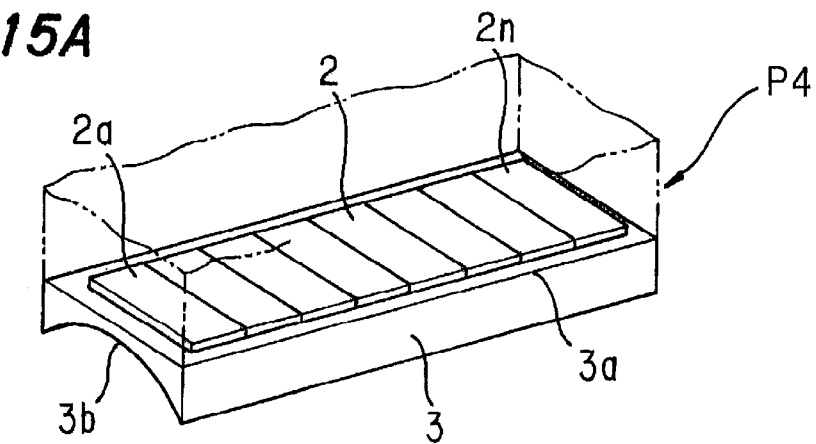
FIG. 15A and FIG. 15B are a fragmentary perspective view of an ultrasonic probe according to a fourth example of the ultrasonic probe according to the first embodiment, as viewed from the side of its top wall, and a fragmentary perspective view of the ultrasonic probe as viewed from the side of its bottom wall.
Figure 15B:
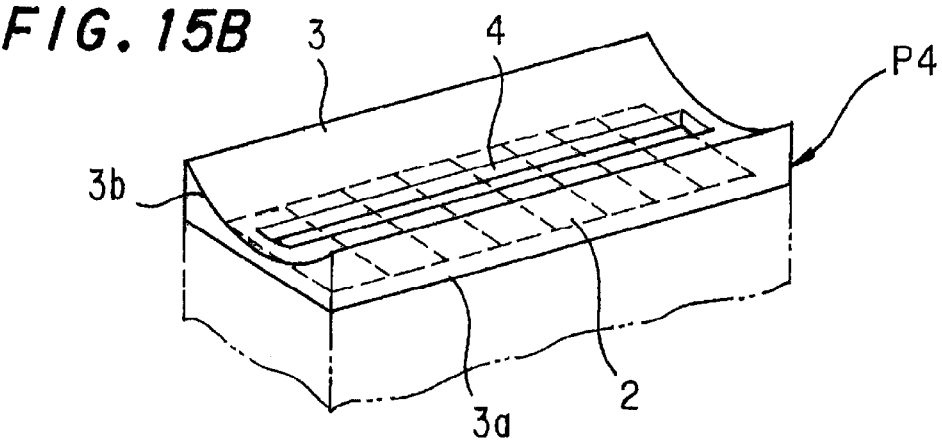
Figure 16:
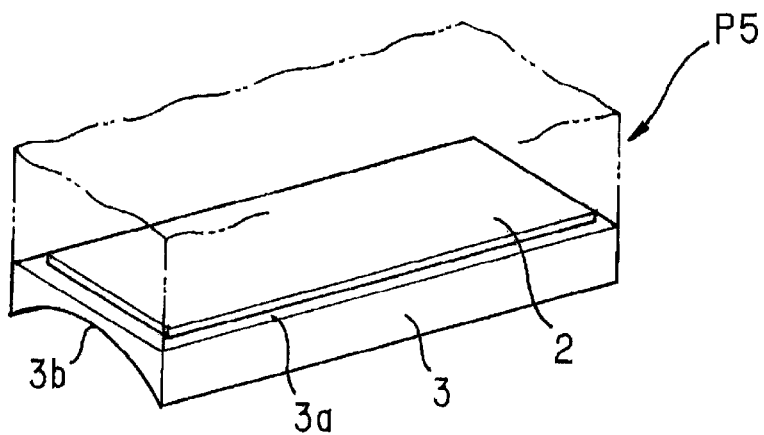
FIG. 16 is a fragmentary perspective view of an ultrasonic probe according to a fifth example of the ultrasonic probe according to the first embodiment, as viewed from the side of its top wall.
Figure 17A:
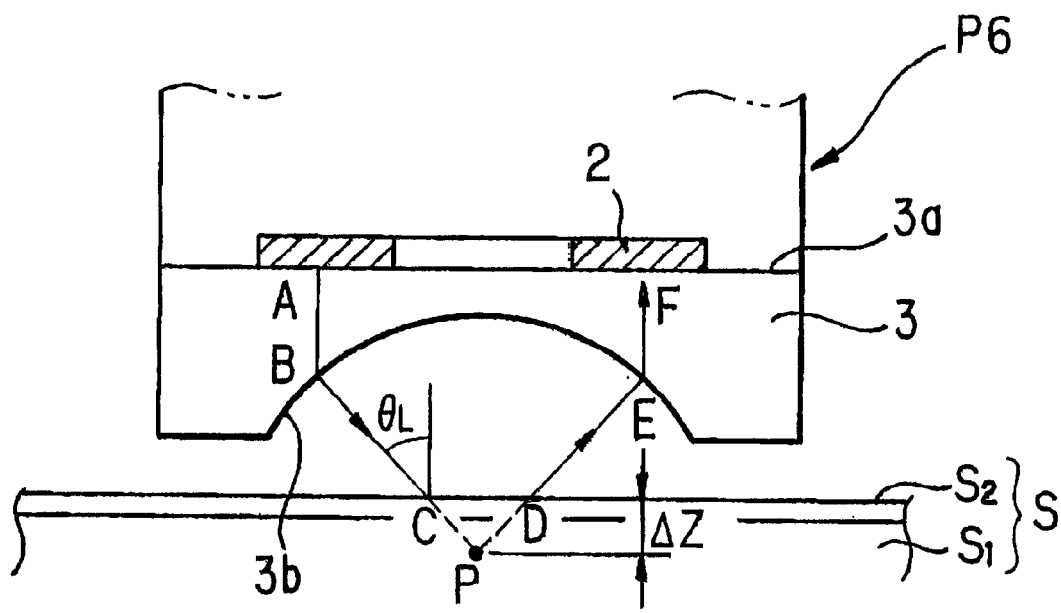
FIG. 17A and FIG. 17B are a fragmentary cross-sectional view and a plan view of a sixth example of the ultrasonic probe according to the first embodiment.
Figure 17B:
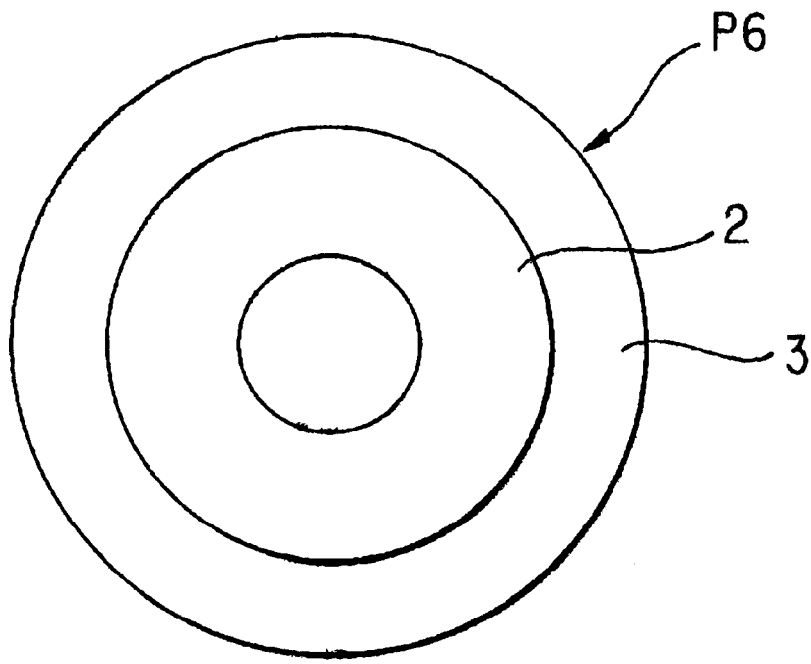
Figure 18A:
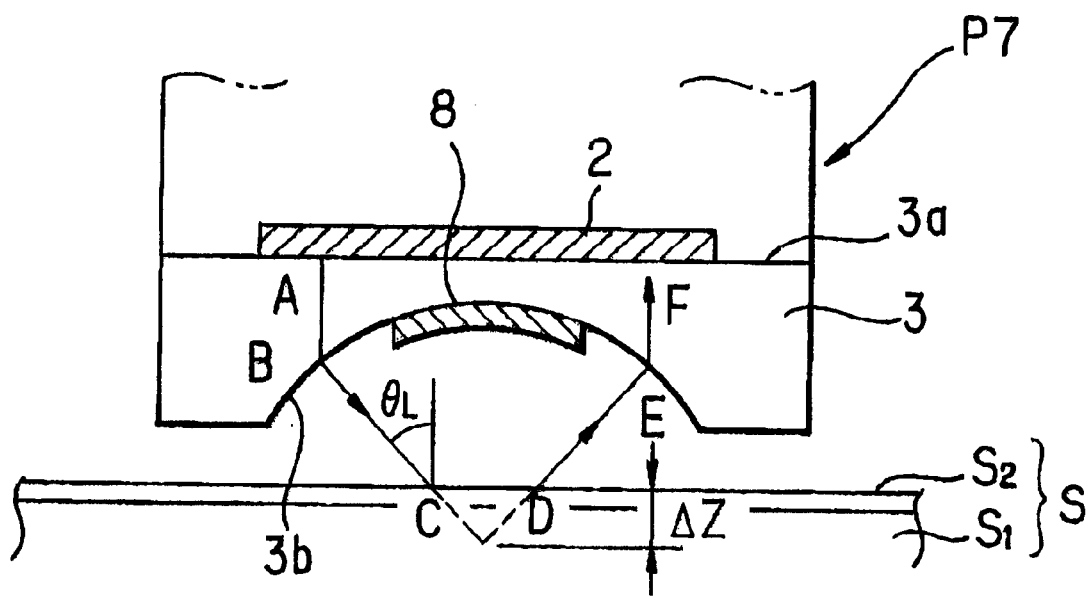
FIG. 18A and FIG. 18B are a fragmentary cross-sectional view and a plan view of a seventh example of the ultrasonic probe according to the first embodiment.
Figure 18B:
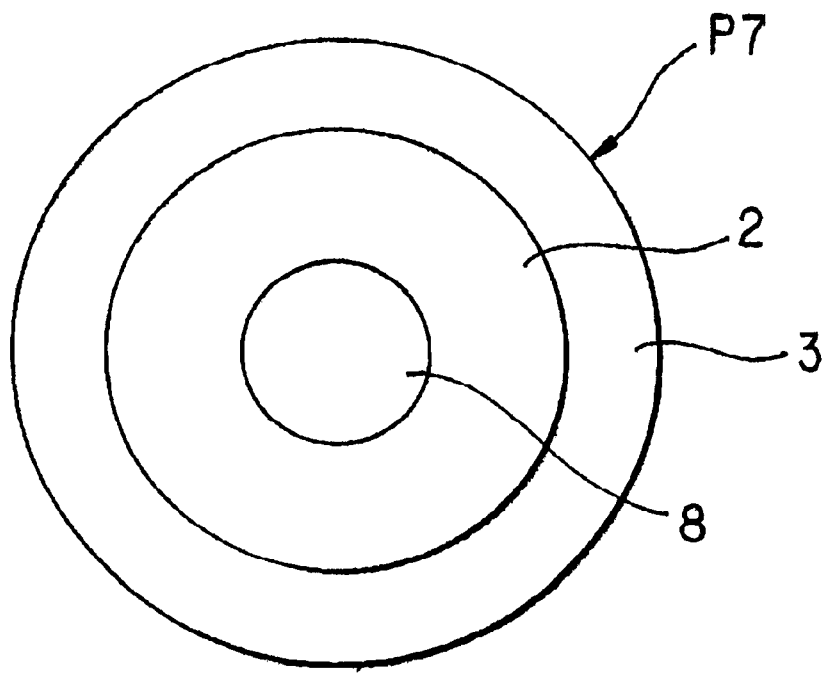
Figure 19A:
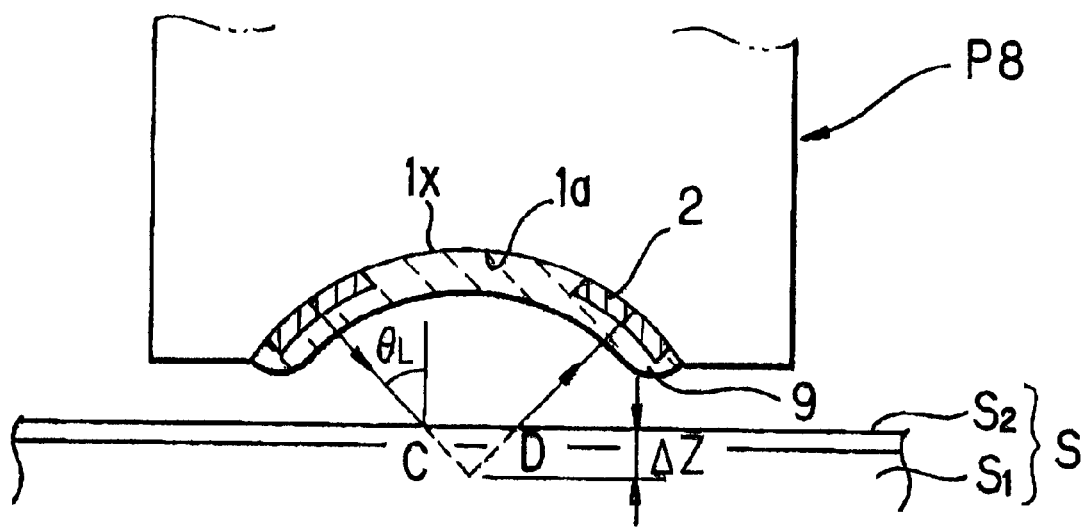
FIG. 19A and FIG. 19B are a fragmentary cross-sectional view and a plan view of an eighth example of the ultrasonic probe according to the first embodiment.
Figure 19B:
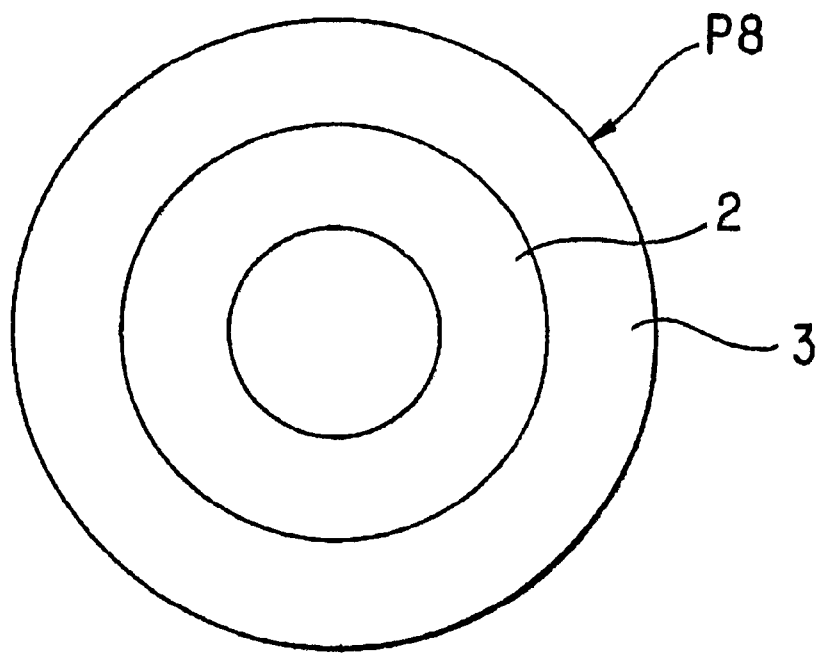
Figure 20A:
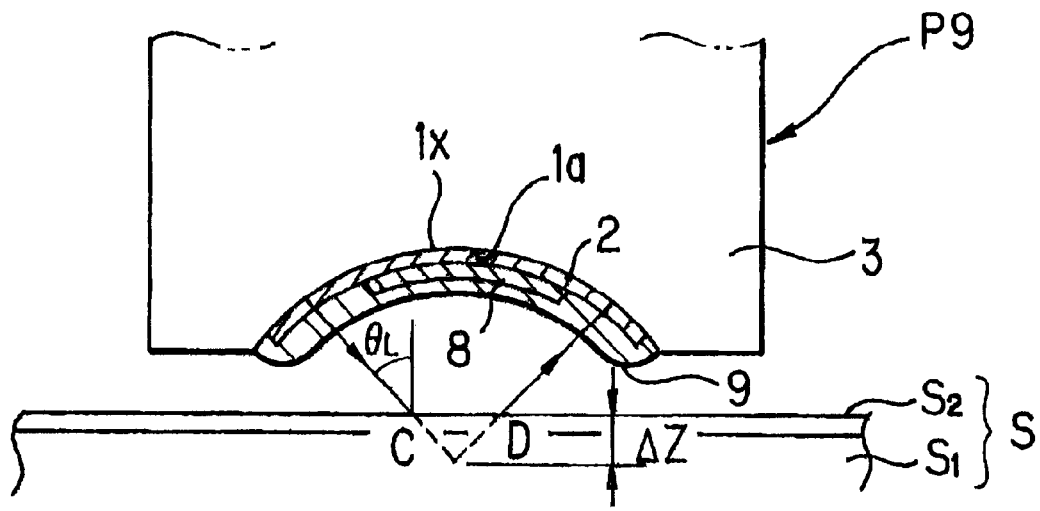
FIG. 20A and FIG. 20B are a fragmentary cross-sectional view and a plan view of a ninth example of the ultrasonic probe according to the first embodiment.
Figure 20B:
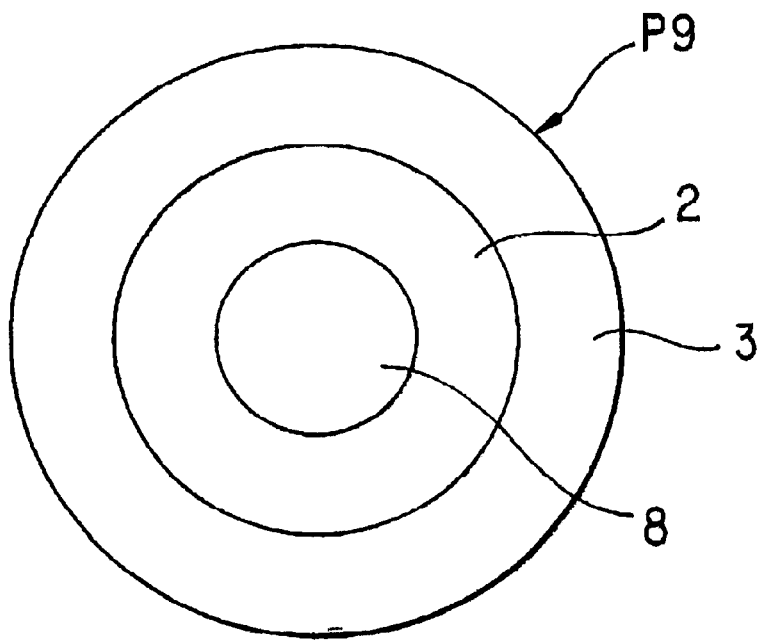
Figure 21A:
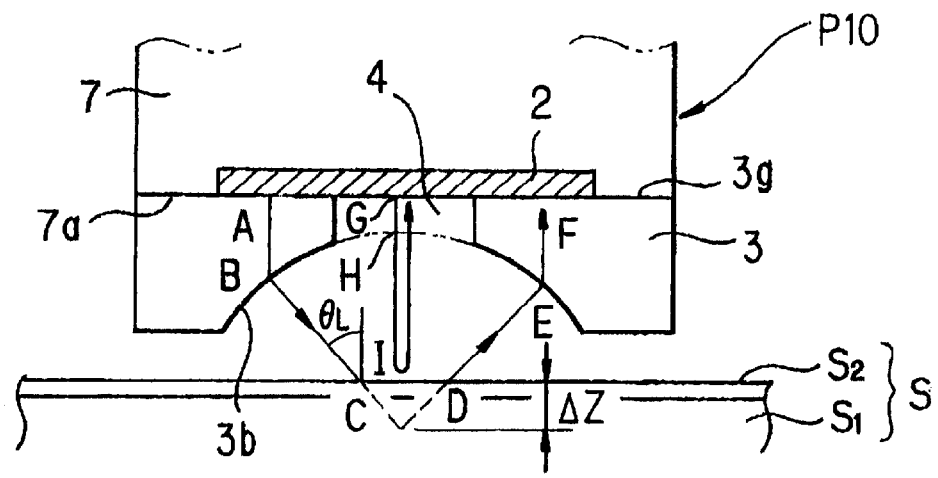
FIG. 21A and FIG. 21B are a fragmentary cross-sectional view and a plan view of a first example of the ultrasonic probe according to the second embodiment.
Figure 21B:
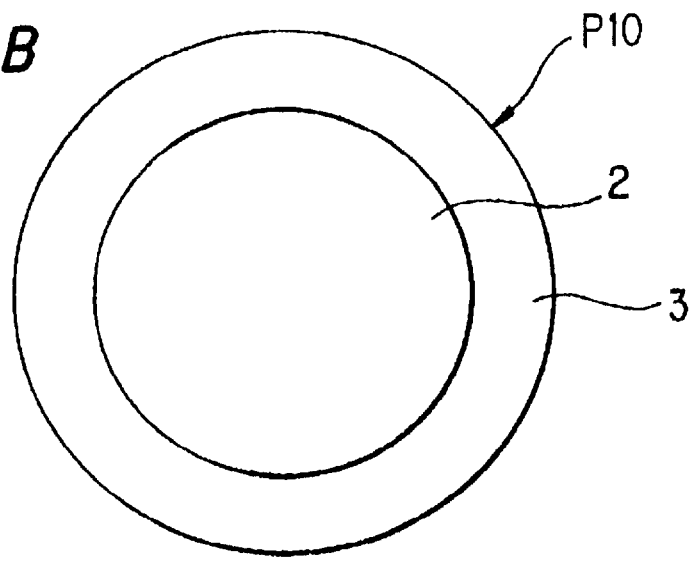
Figure 22:
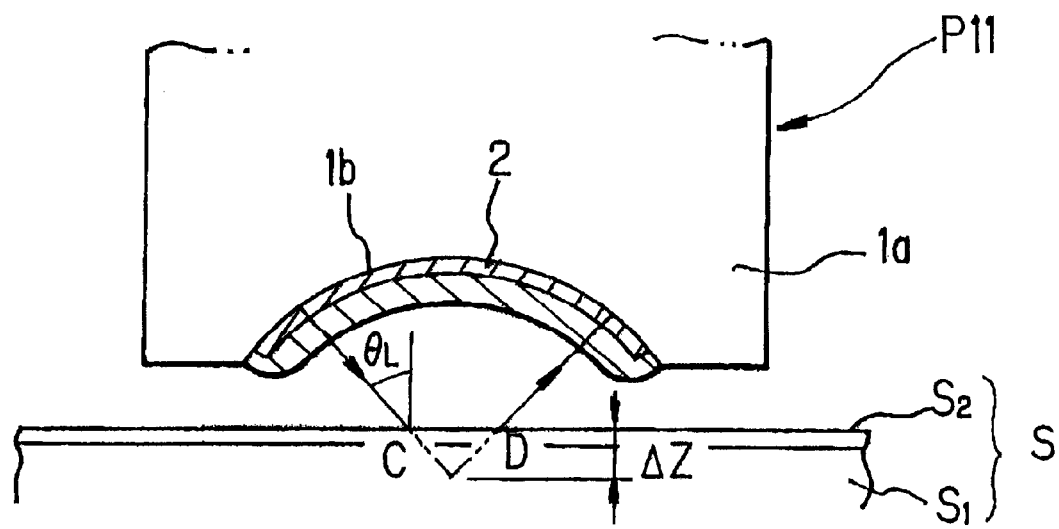
FIG. 22 is a fragmentary cross-sectional view of an ultrasonic probe according to a second example of the second embodiment.
Figure 23:
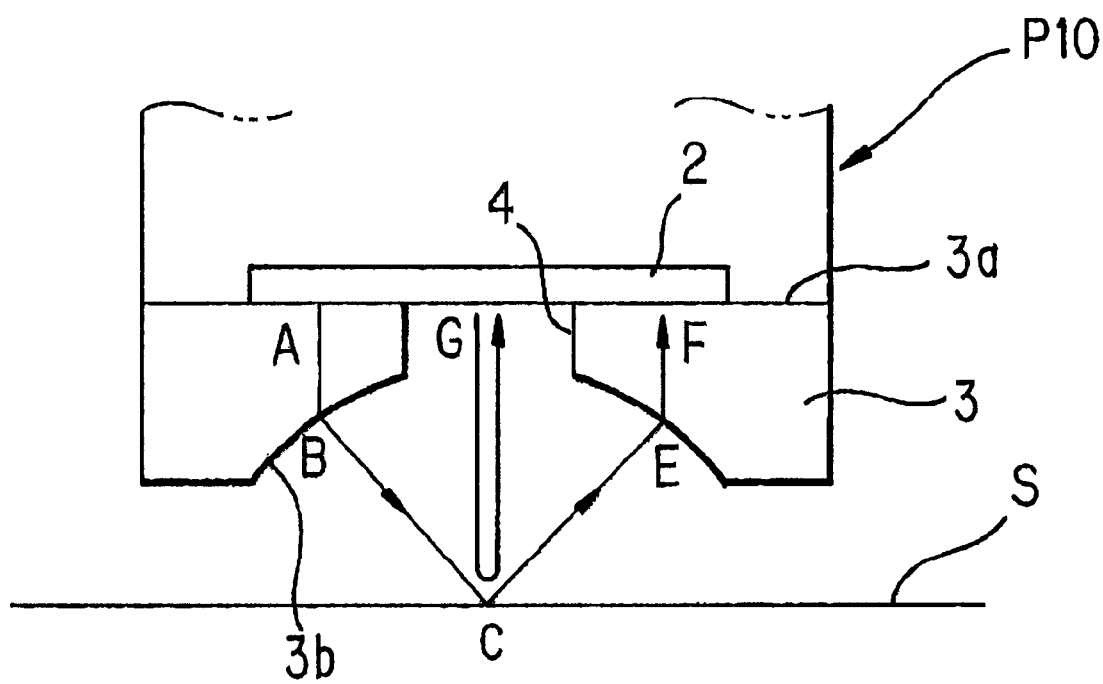
FIG. 23 is a schematic illustration showing a state when a focal point of an acoustic lens has been brought into registration with a surface of a specimen.
Figure 24:
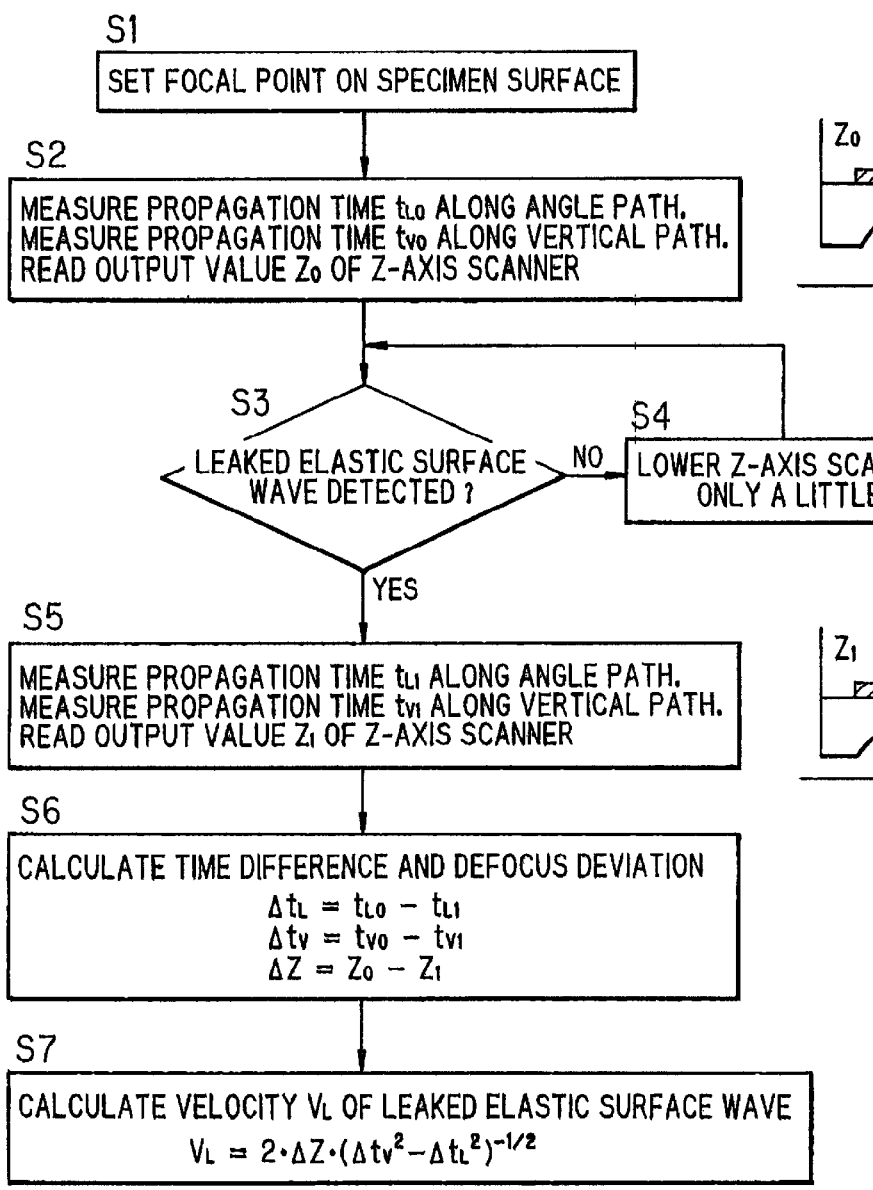
FIG. 24 is a flow chart illustrating processing procedures of an ultrasonic inspection method.
Figure 25A:
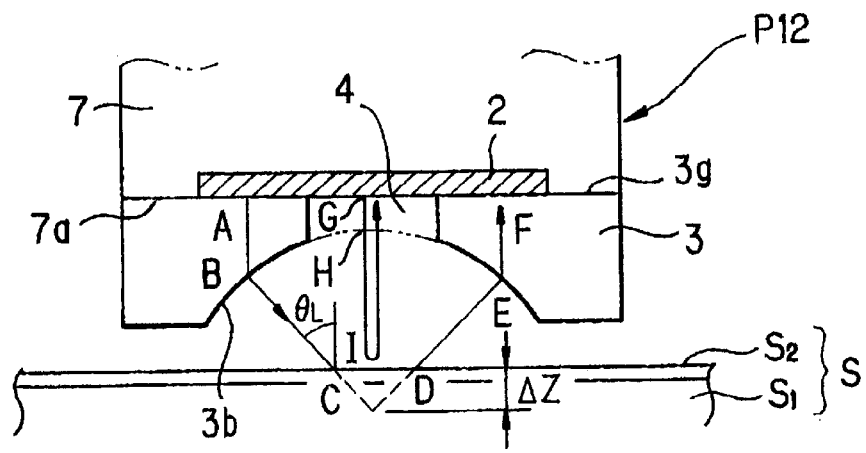
FIG. 25A and FIG. 25B are a fragmentary cross-sectional view and a plan view of an ultrasonic probe according to a first example of the third embodiment.
Figure 25B:
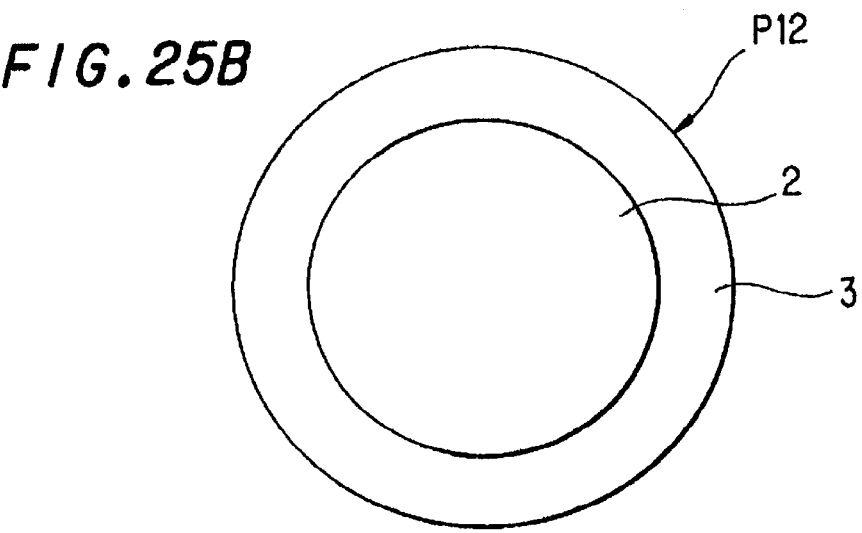
Figure 26:
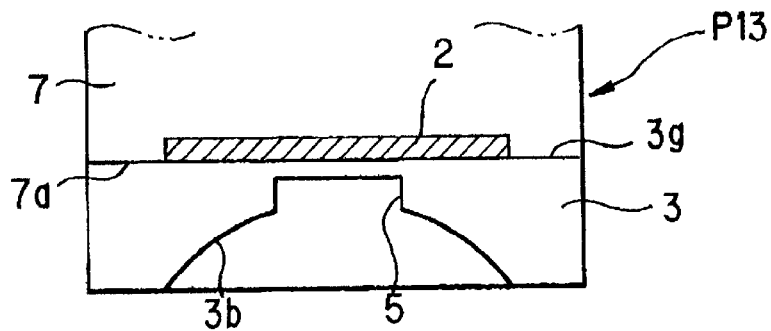
FIG. 26 is a fragmentary cross-sectional view of an ultrasonic probe according to a third example of the third embodiment.
Figure 27A:
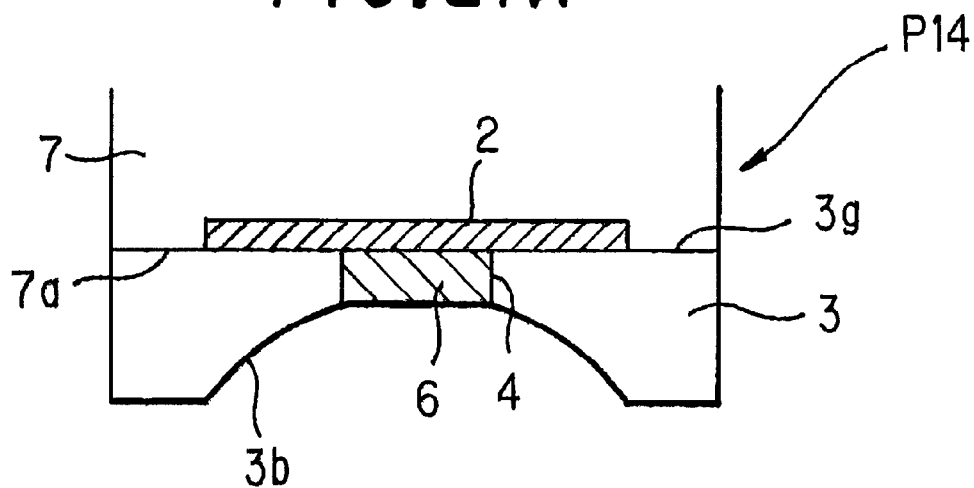
FIG. 27A, FIG. 27B and FIG. 27C are fragmentary cross-sectional views of an ultrasonic probe according to a third example of the third embodiment.
Figure 27B:
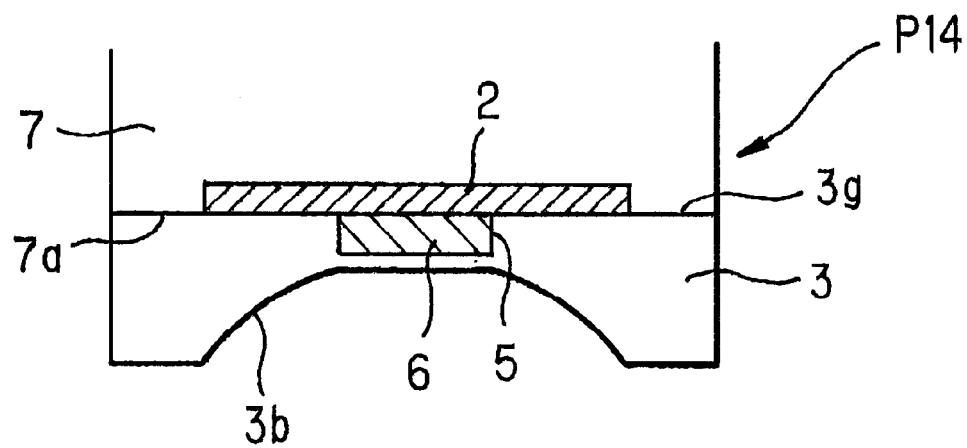
Figure 27C:
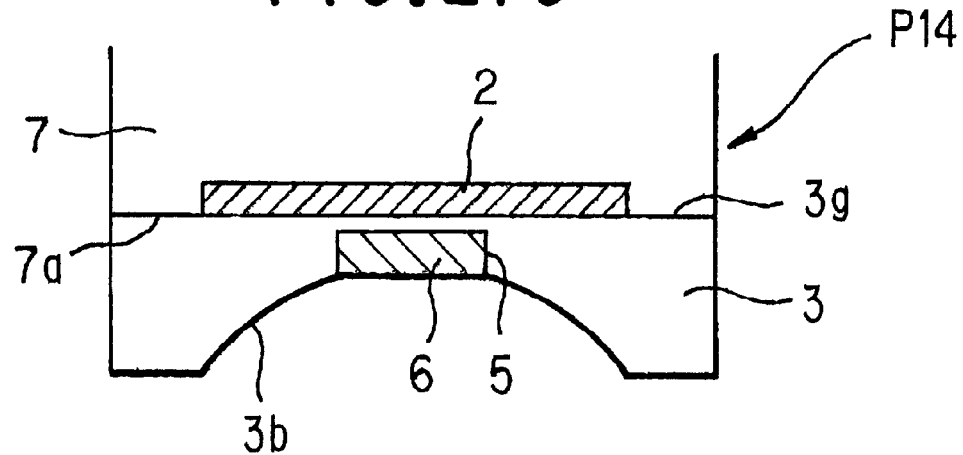
Figure 28A:
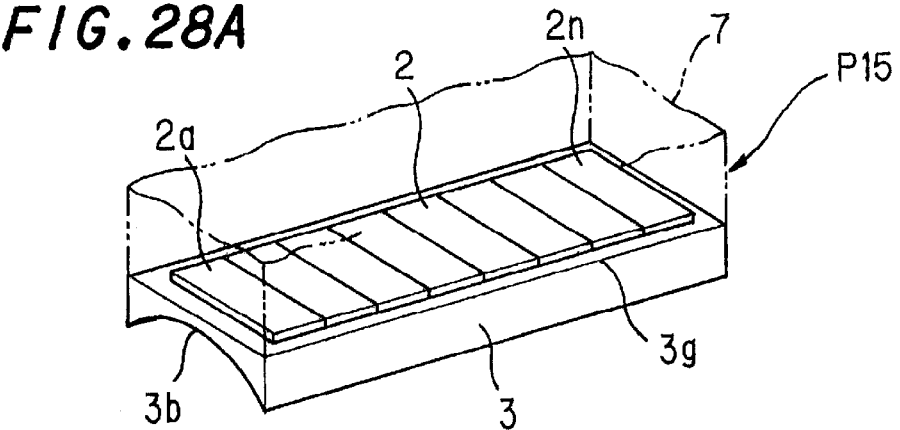
FIG. 28A and FIG. 28B are a perspective view of an ultrasonic probe according to a fourth example of the third embodiment, as viewed from the side of its top wall, and a perspective view of the ultrasonic probe as viewed from the side of its bottom wall.
Figure 28B:
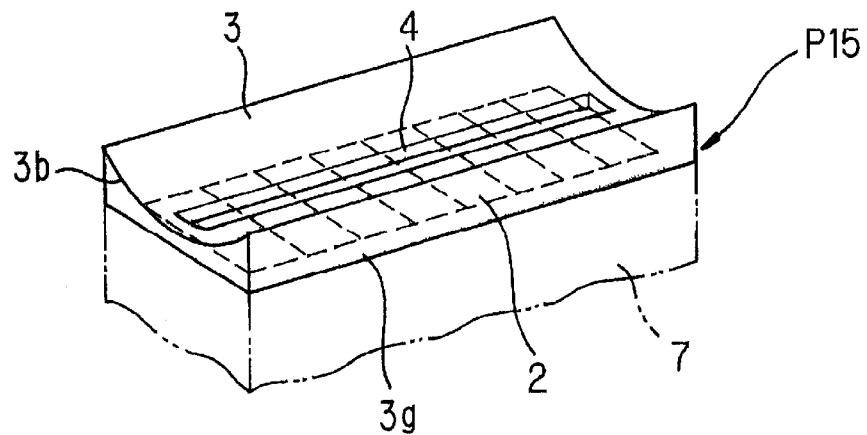
Figure 29:
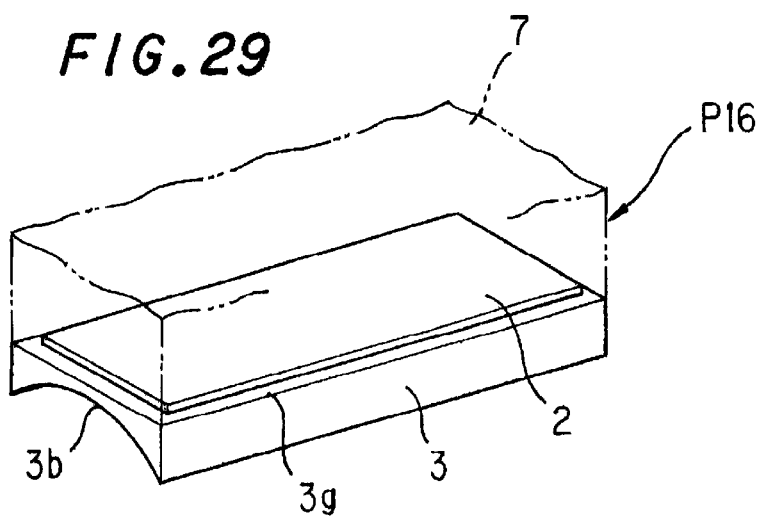
FIG. 29 is a perspective view of an ultrasonic probe according to a fifth example of the third embodiment, as viewed from the side of its top wall.
Figure 30:
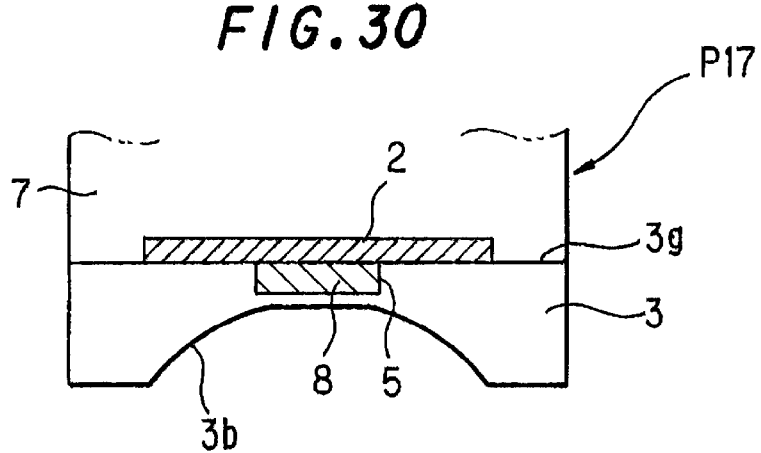
FIG. 30 is a fragmentary cross-sectional view of an ultrasonic probe according to a sixth example of the third embodiment.
Figure 31A:
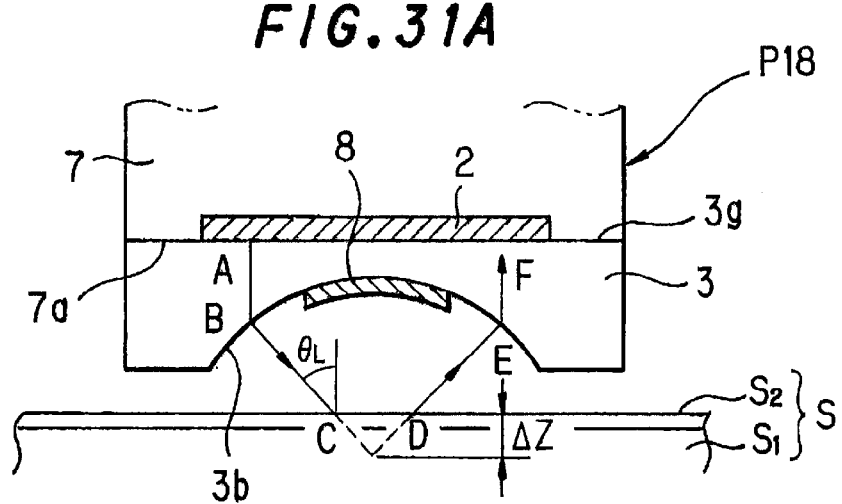
FIG. 31A and FIG. 31B are a fragmentary cross-sectional view and a plan view of an ultrasonic probe according to a seventh example of the third embodiment.
Figure 31B:
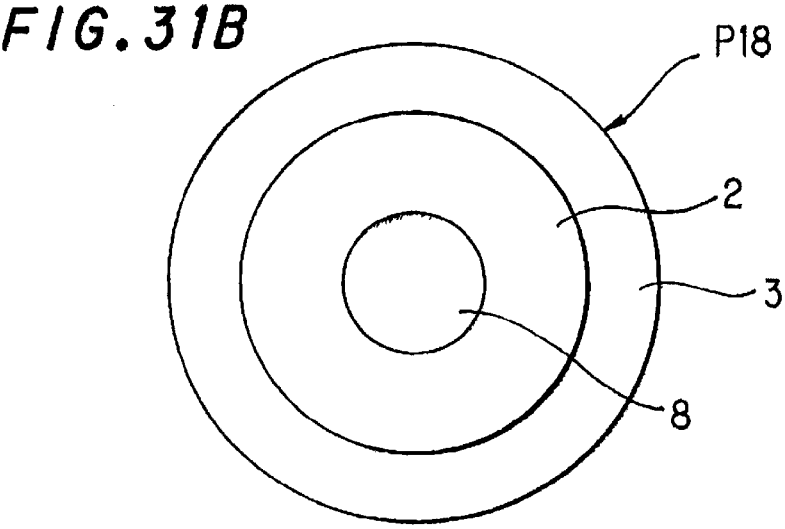
Figure 32:
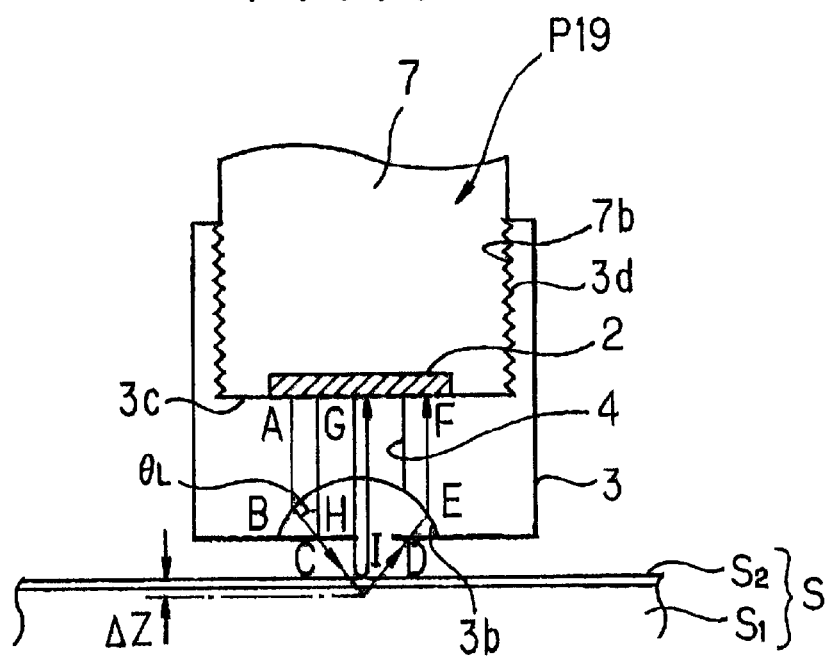
FIG. 32 is a fragmentary cross-sectional view of an ultrasonic probe according to an eighth example of the third embodiment.
Figure 33:
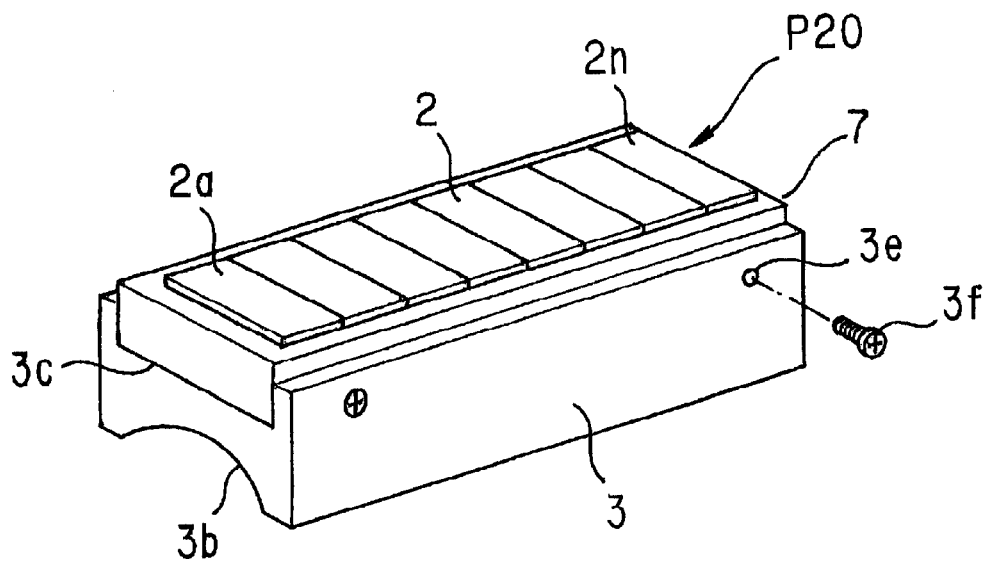
FIG. 33 is a perspective view of an ultrasonic probe according to a ninth example of the third embodiment.
Figure 34A:
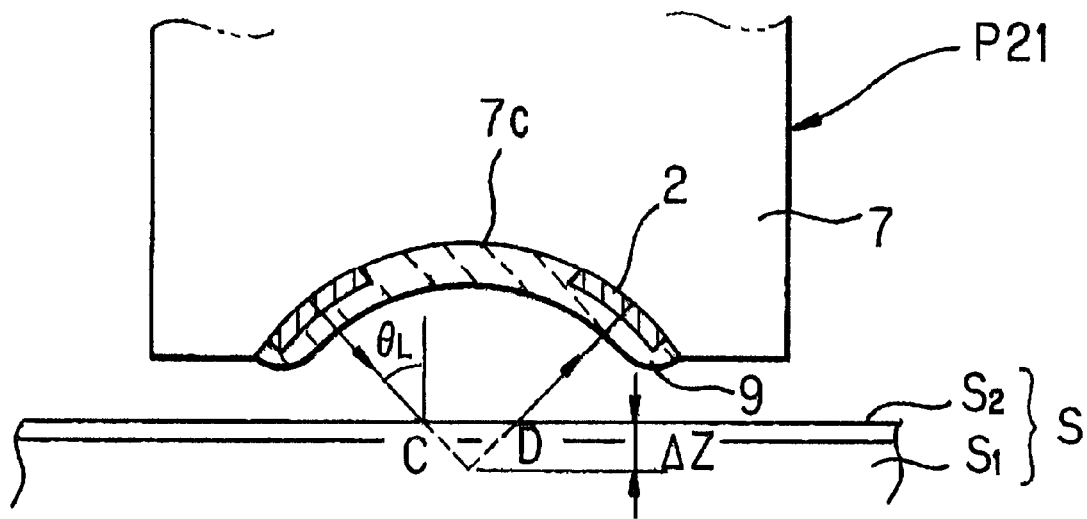
FIG. 34A and FIG. 34B are a fragmentary cross-sectional view and a plan view of an ultrasonic probe according to a tenth example of the third embodiment.
Figure 34B:
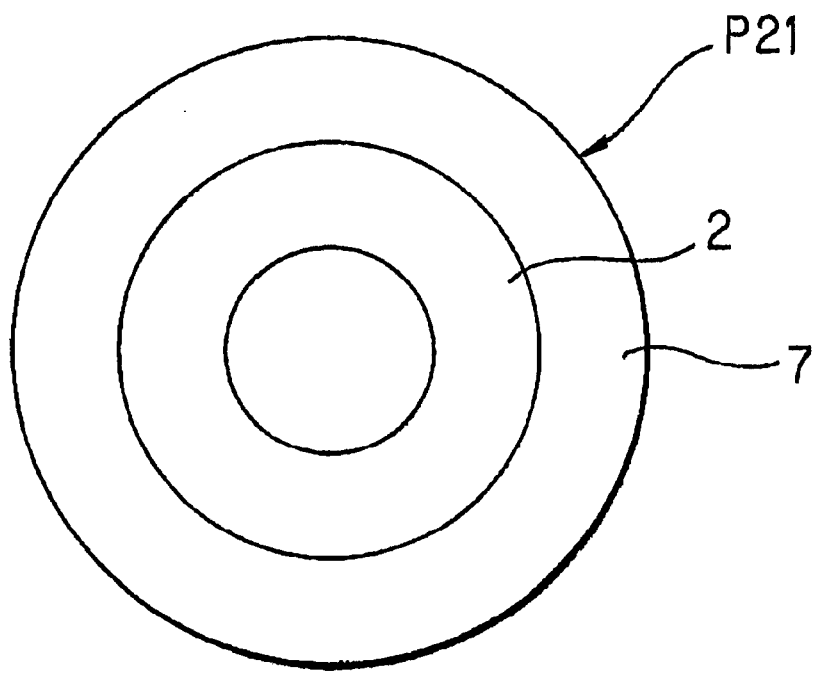
Figure 35A:
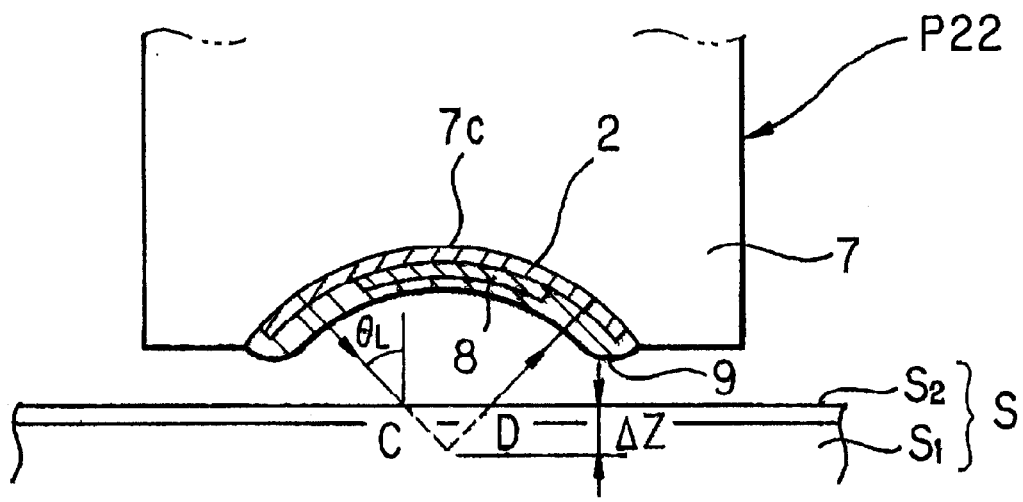
FIG. 35A and FIG. 35B are a fragmentary cross-sectional view and a plan view of an ultrasonic probe according to an eleventh example of the third embodiment.
Figure 35B:
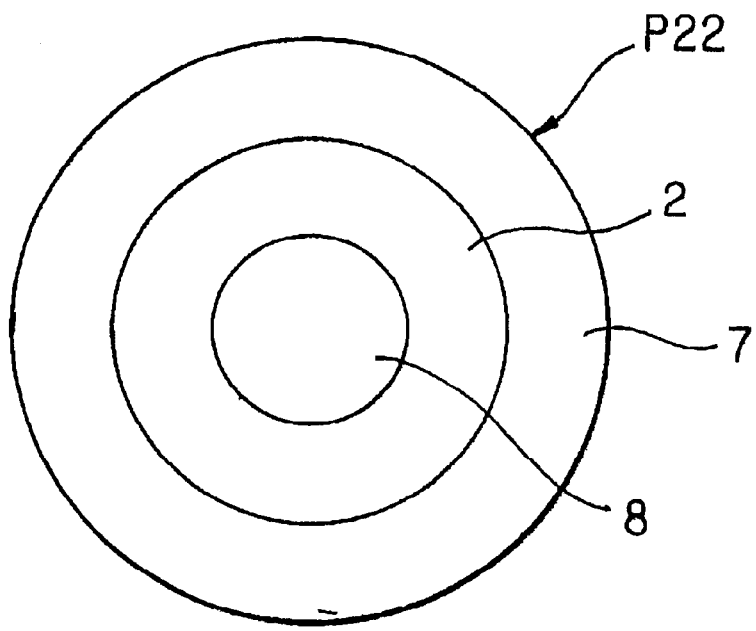
Figure 36A:
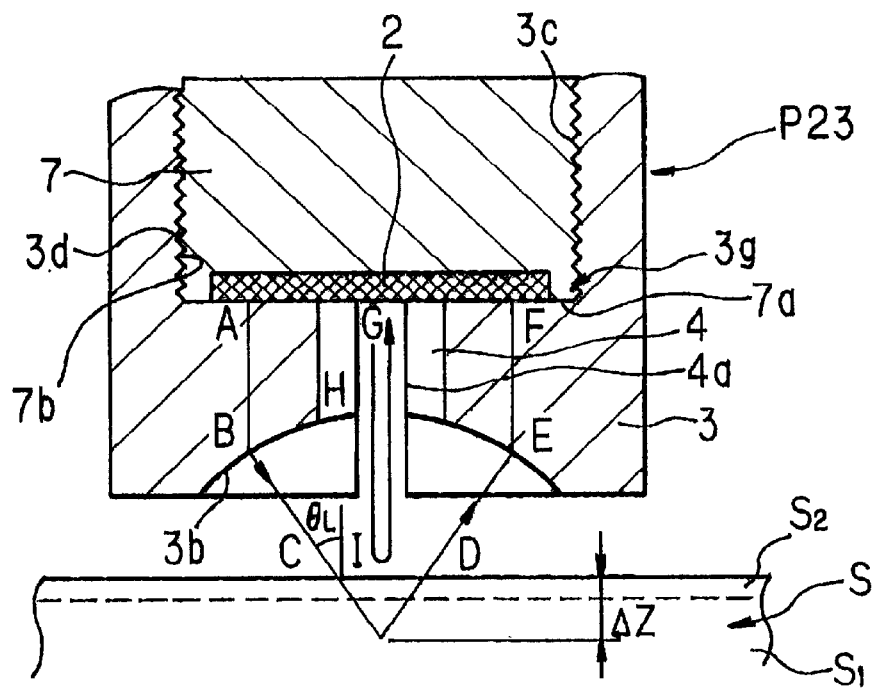
FIG. 36A and FIG. 36B are a fragmentary cross-sectional view and a plan view of an ultrasonic probe according to a first example of the fourth embodiment.
Figure 36B:
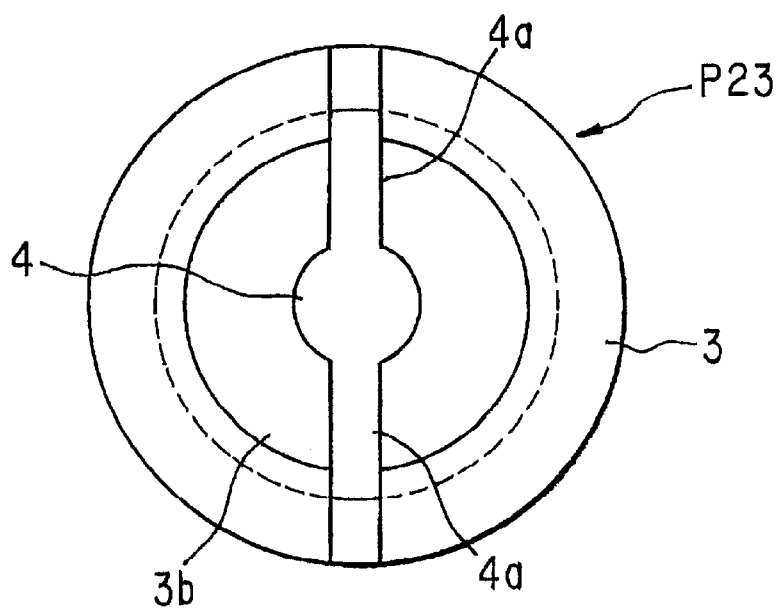
Figure 37:
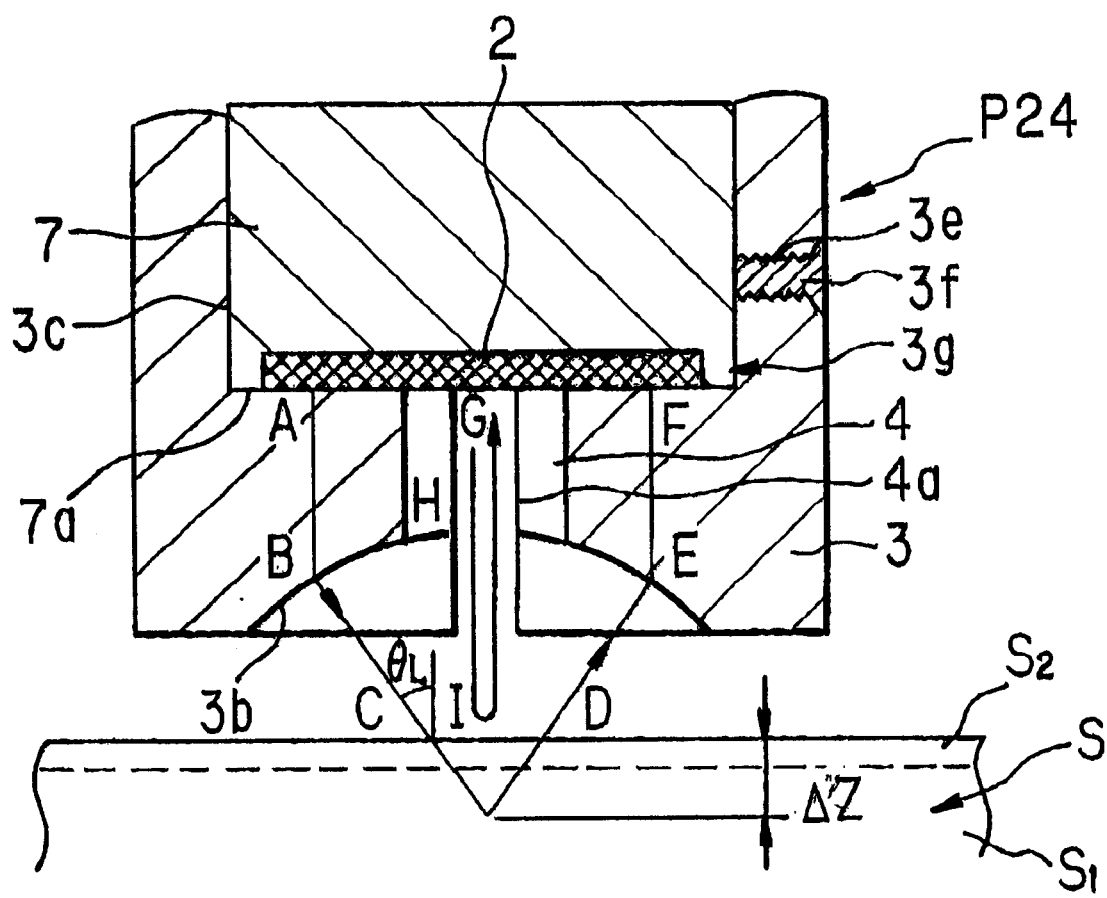
FIG. 37 is a cross-sectional view illustrating another example of a method for connecting a flat ultrasonic probe and an acoustic lens together.
Figure 38A:
FIG. 38A and FIG. 38B are pictures showing illustrative C-scope images of leaked waves in the first example of the fourth embodiment.
Figure 38B:
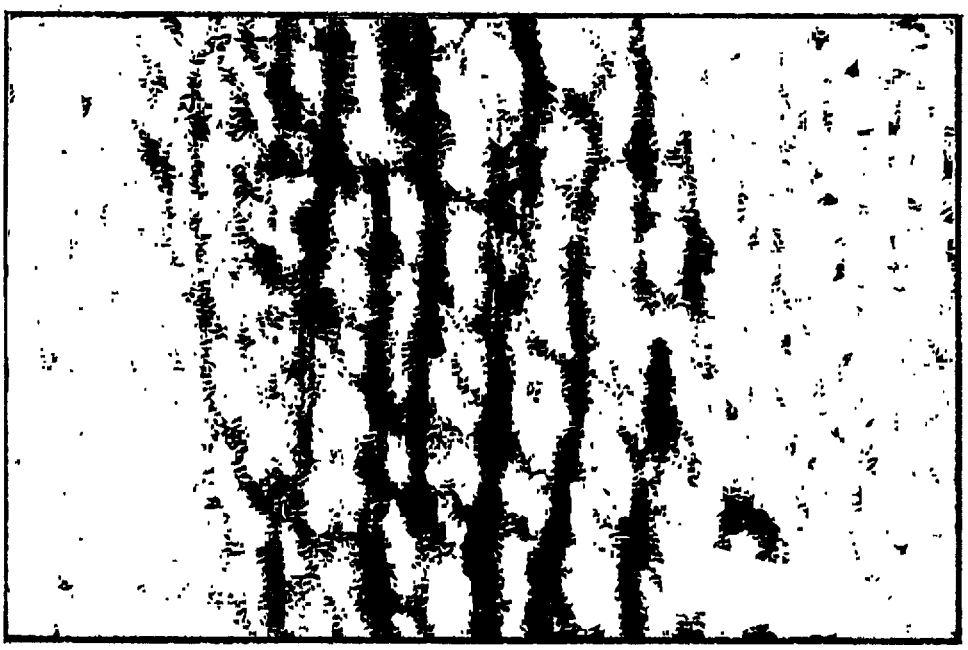
Figure 39A:
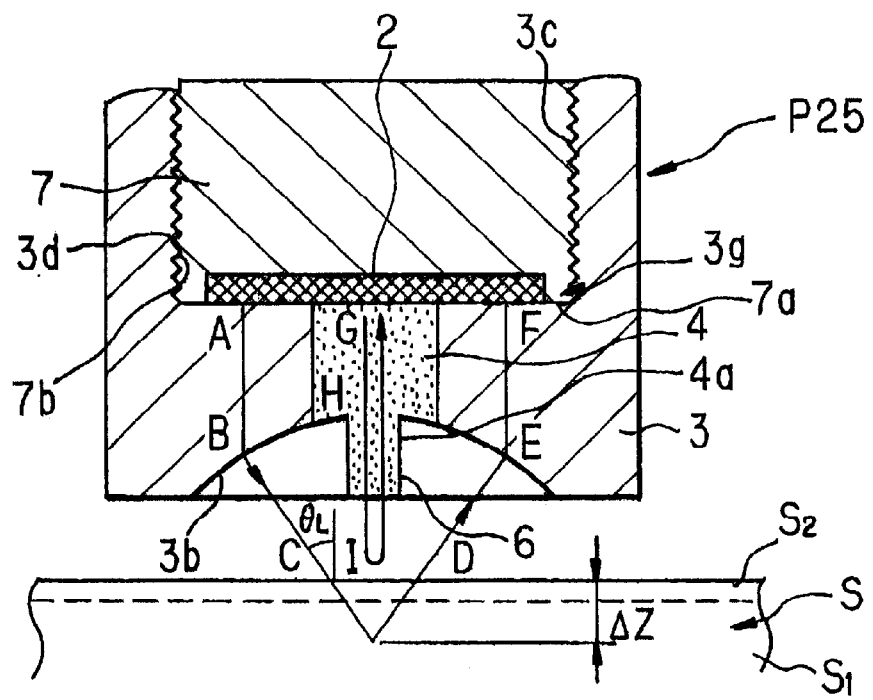
FIG. 39A and FIG. 39B are a fragmentary cross-sectional view and a plan view of an ultrasonic probe according to a second example of the fourth embodiment.
Figure 39B:
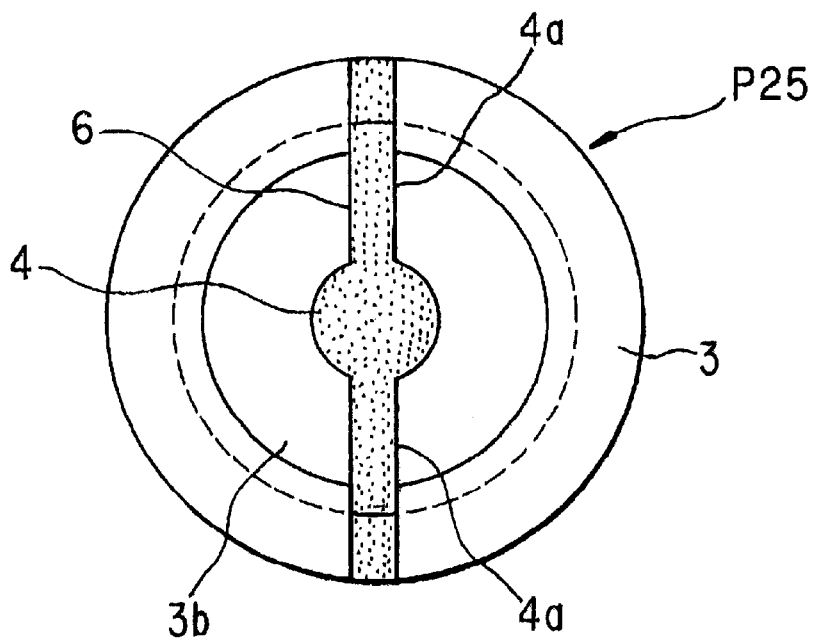
Figure 40A:
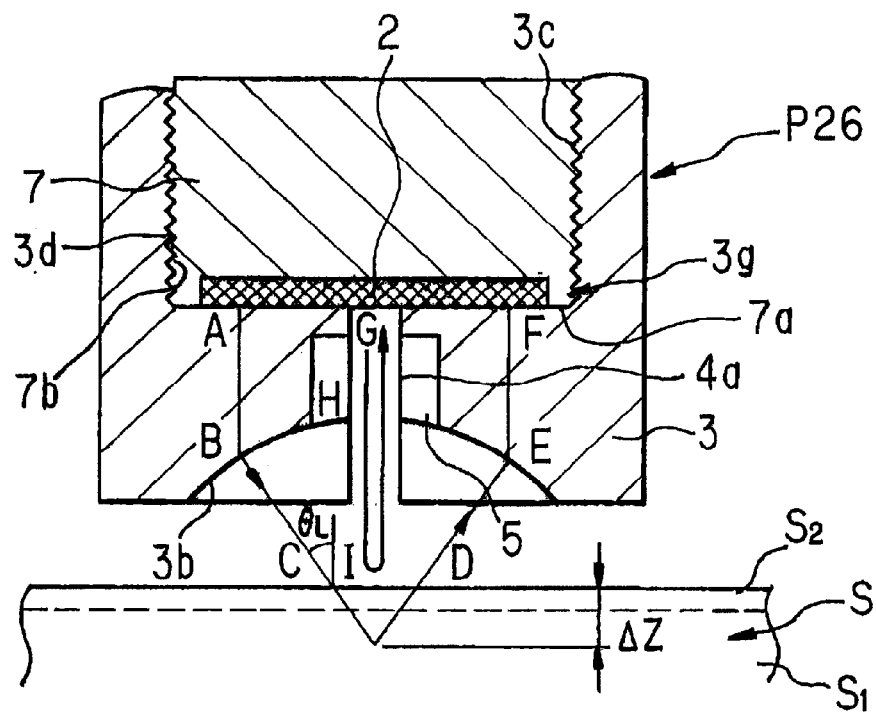
FIG. 40A and FIG. 40B are a fragmentary cross-sectional view and a plan view of an ultrasonic probe according to a third example of the fourth embodiment.
Figure 40B:
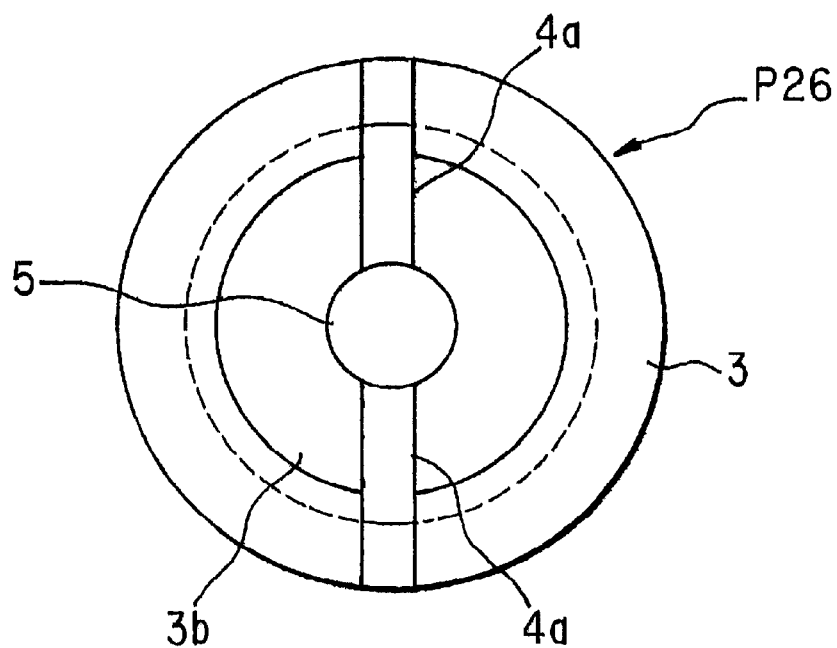
Figure 41A:
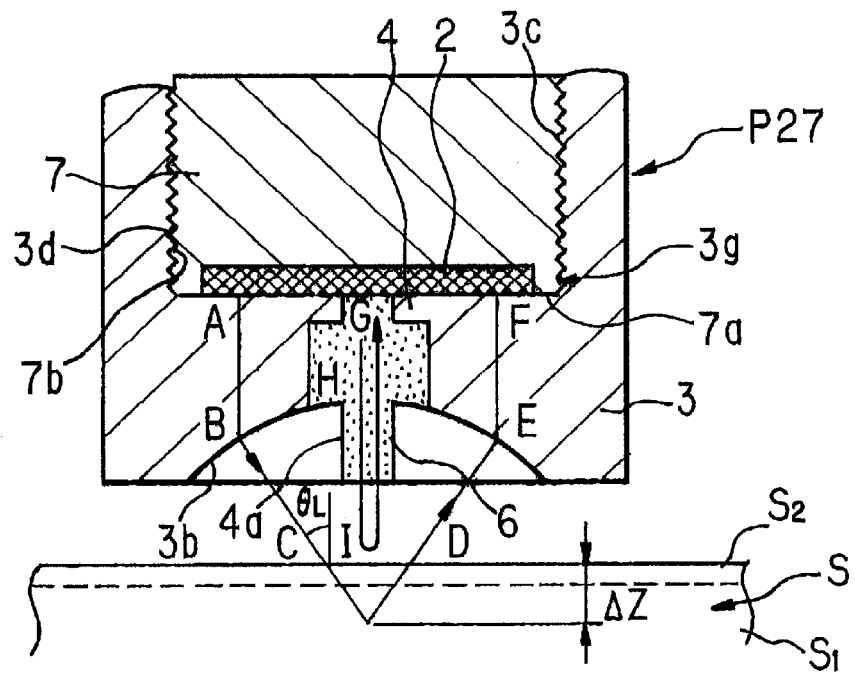
FIG. 41A and FIG. 41B are a fragmentary cross-sectional view and a plan view of an ultrasonic probe according to a fourth example of the fourth embodiment.
Figure 41B:
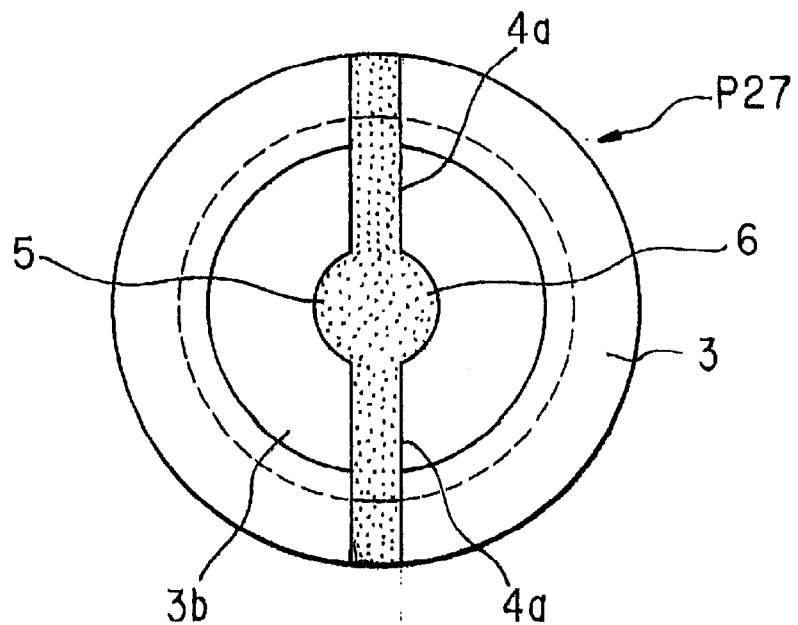
Figure 42A:
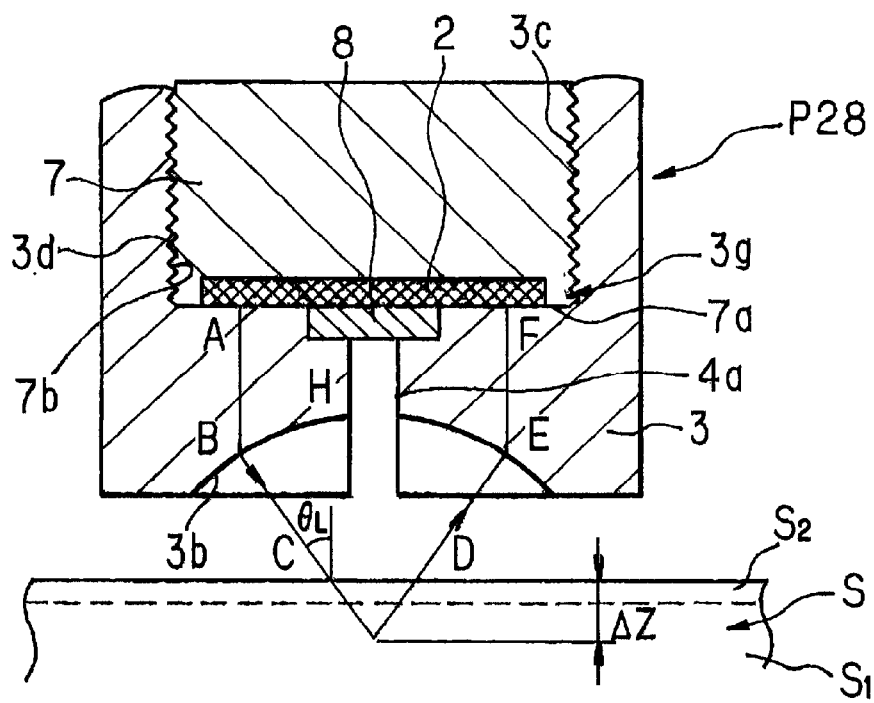
FIG. 42A and FIG. 42B are a fragmentary cross-sectional view and a plan view of an ultrasonic probe according to a fifth example of the fourth embodiment.
Figure 42B:
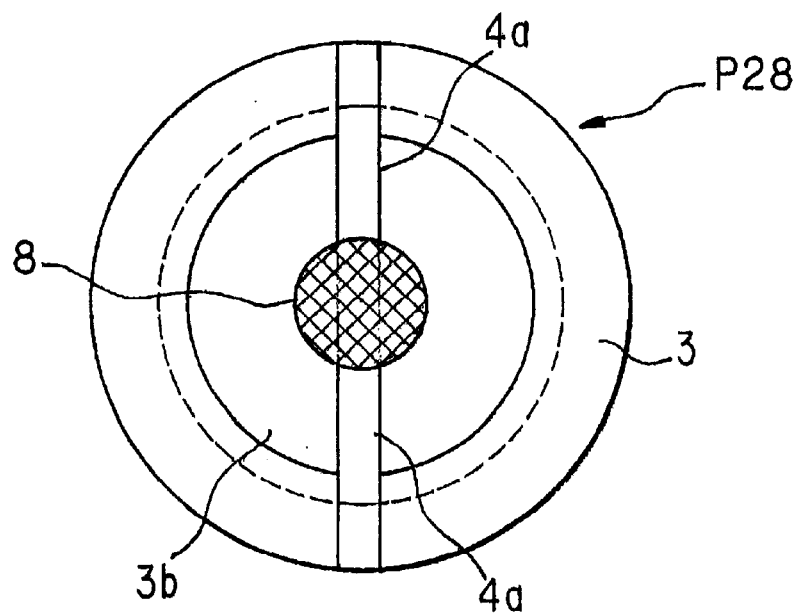
Figure 43:
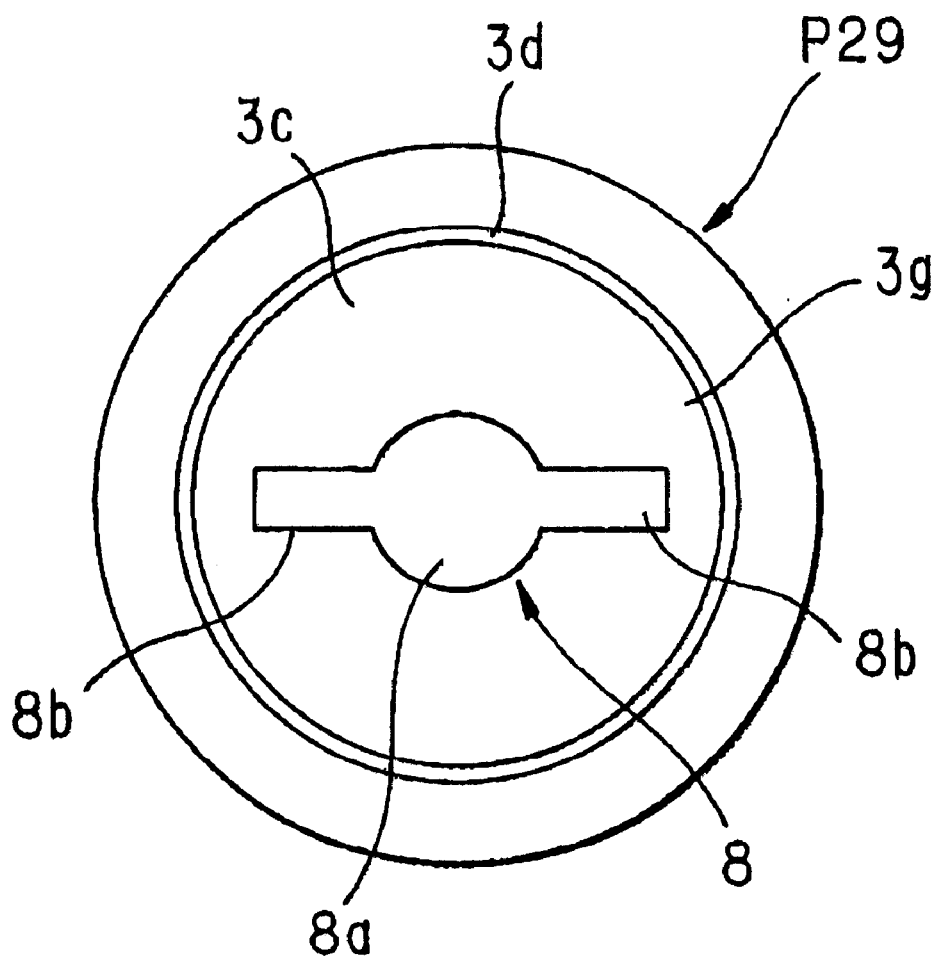
FIG. 43 is a plan view of an ultrasonic probe according to a sixth example of the fourth embodiment.
Figure 44A:
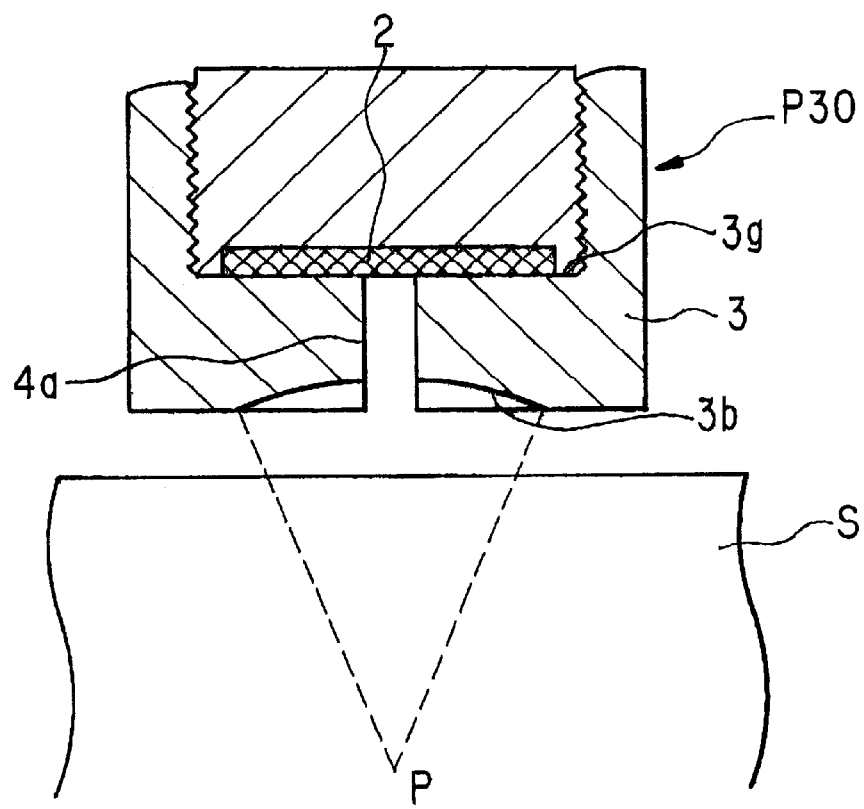
FIG. 44A and FIG. 44B are a fragmentary cross-sectional view and a plan view of an ultrasonic probe according to a seventh example of the fourth embodiment.
Figure 44B:
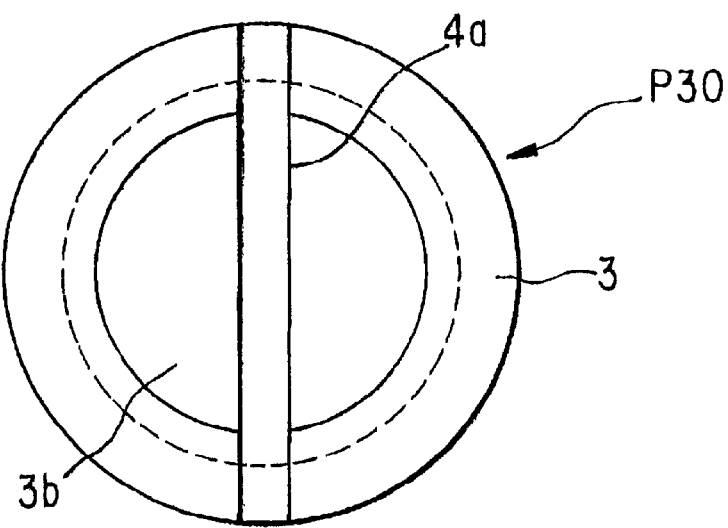

When an ultrasonic probe 101 provided with an acoustic lens 103 which does not have the through-hole 4 is used as shown in FIGS. 12A and 12B, the aluminum-made acoustic lens 3 having the high ultrasonic wave propagation speed and water having the low ultrasonic wave propagation are interposed between the angle paths A→B→C and D→E→F of the oscillator 2 and the specimen S and also between the vertical paths G→(H)→I and I→(H)→G of the oscillator 102 and the specimen S. Accordingly, the propagation time of the angled incident wave, leaked elastic surface wave and leaked wave along the path A→B→C→D→E→F and the propagation time of the vertical incident wave and vertical reflection wave along the path G→(H)→I→(H)→G become substantially the same. An echo waveform L of a leaked wave is buried in an echo waveform V of a vertical reflection wave, thereby making it difficult to separate those waveforms from each other and hence, failing to determine the echo level of the leaked wave.

Described specifically, a difference in propagation time between both echo waveforms will be determined under the same conditions as the ultrasonic probe of this embodiment. The propagation time of a vertical incident wave and a vertical reflection wave along the path G→H→I→H→G shown in FIG. 12A is 10.05 µs, while the propagation time of an angled incident wave, a leaked elastic surface wave and a leake wave along the path A→B→C→D→E→F depicted in FIG. 12A is 10.1 µs. Their difference is, therefore, 50 ns, that is, only a half of the period (100 ns) of the frequency used. Even if the weak leaked wave has been received, the echo waveform L of the leaked wave is buried in the echo waveform V of the vertical reflection wave so that the echo level of the leaked wave cannot be determined.

What is claimed is:

1. An ultrasonic inspection device provided with an ultrasonic scanning unit for scanning a surface of a specimen with an ultrasonic wave through a medium for the ultrasonic wave, a drive unit for said ultrasonic scanning unit, and a computing unit for controlling said ultrasonic scanning unit via said drive unit and performing a flaw detection of a surface layer of said specimen, comprising:

an ultrasonic probe, an oscillator, and an acoustic lens having propagation paths for a vertical incident wave and an angled incident wave to said specimen and propagation paths for a vertical reflection wave and a leaked wave from said specimen such that a propagating speed of an ultrasonic wave along said propagation path for said vertical incident wave and said propagation path for said vertical reflection wave and a propagating speed of an ultrasonic wave along said propagation path for said angled incident wave and said propagation path for said leaked wave differ from each other, said ultrasonic probe being arranged in said ultrasonic scanning unit to perform transmission of an angled incident wave, which induces a leaked elastic surface wave, to said specimen and reception of a leaked wave from said specimen, whereby soundness of said surface layer of said specimen is evaluated at said computing unit from a level of said leaked wave received by said ultrasonic probe.

2. An ultrasonic inspection device according to claim 1, wherein said acoustic lens is provided with a through-hole which extends from a setting surface for said oscillator to a lens curvature surface, which is located opposite said setting surface, along said propagation paths for said vertical incident wave and vertical reflection wave.

3. An ultrasonic inspection device according to claim 2, wherein said through-hole is filled with a filler made of a material different in the propagating speed of an ultrasonic wave from a material which forms said propagation paths for said angled incident wave and leaked wave.

4. An ultrasonic inspection device according to claim 1, wherein said oscillator is formed in a ring shape in plan such that said ultrasonic probe is capable of performing transmission of an angled incident wave to said specimen and reception of a leaked wave from said specimen but is incapable of performing transmission of a vertical incident wave to said specimen and reception of a vertical reflection wave from said specimen.

5. An ultrasonic inspection device according to claim 1, wherein said ultrasonic probe is provided with an oscillator formed in a disc shape in plan, an ultrasonic wave shielding material arranged at a central part of a transmission/reception side of said oscillator, said ultrasonic probe is capable of performing transmission of an angled incident wave to said specimen and reception of a leaked wave from said specimen but is incapable of performing transmission of a vertical incident wave to said specimen and reception of a vertical reflection wave from said specimen.

6. An ultrasonic inspection device provided with an ultrasonic scanning unit, a drive unit for said ultrasonic scanning unit, and a computing unit for controlling said ultrasonic scanning unit via said drive unit and performing a desired ultrasonic inspection, said ultrasonic scanning unit having an ultrasonic probe and a mechanical scanner for moving said ultrasonic probe relative to a specimen, wherein based on a difference between a propagation time of a first angled incident wave, a first leaked elastic surface wave and a first leaked wave when a first ultrasonic wave is transmitted with a focal point of said ultrasonic probe being set at a first depth position is said specimen and a propagation time of a second angled incident wave, a second leaked elastic surface wave and a second leaked wave when a second ultrasonic wave is transmitted with said focal point of said ultrasonic probe being set at a second depth position in said specimen and also on a difference between a propagation time of first vertical incident wave and a first vertical reflection wave when said first ultrasonic wave is transmitted with said focal point of said ultrasonic probe being set at said first depth position in said specimen and a propagation time of a second vertical incident wave and a second vertical reflection wave when said second ultrasonic wave is transmitted with said focal point of said ultrasonic probe being set at said second depth position in said specimen, a speed of said leaked elastic surface wave is calculated at said computing unit.

7. An ultrasonic inspection device according to claim 6, wherein:

said ultrasonic probe has an oscillator and an acoustic lens for causing an ultrasonic wave, which has been transmitted from said oscillator, to converge and then to enter said specimen; and a propagation speed of an ultrasonic wave along propagation paths of said acoustic lens for a vertical incident wave and a vertical reflection wave is different from a propagation speed of an ultrasonic wave along propagation paths of said acoustic lens for an angled incident wave and a leaked wave.

8. An ultrasonic inspection device according to claim 7, wherein said acoustic lens is provided with a through-hole which extends from a setting surface for said oscillator to a lens curvature surface, which is located opposite said setting surface, along said propagation paths for said vertical incident wave and vertical reflection wave.

9. An ultrasonic inspection device according to any one of claims 1, 2, 4 and 8, wherein said acoustic lens comprises a cylindrical lens in which a setting surface for said oscillator is formed as a planar surface and a lens curvature surface is formed as an arcuate surface.

10. An ultrasonic inspection device according to claim 6, wherein an oscillator-setting surface of said ultrasonic probe is formed as a spherical surface.

11. A focused ultrasonic probe provided with a flat ultrasonic probe, an oscillator-setting surface of which is formed as a planar surface, and an acoustic lens arranged on a free end portion of said flat ultrasonic probe and adapted to cause ultrasonic waves, which have been transmitted from said oscillator, to converge, wherein said acoustic lens is constructed such that a propagation speed of a first one of said ultrasonic waves along propagation paths for a vertical incident wave to a specimen and a vertical reflection wave from said specimen and a propagation speed of a second one of said ultrasonic waves along propagation paths for an angled incident wave to said specimen and a leaked wave from said specimen differ from each other.

12. A focused ultrasonic probe according to claim 11, wherein aid acoustic lens is provided with a through-hole which extends from said oscillator-setting surface to a lens curvature surface, which is located opposite said oscillator-setting surface, along said propagation paths for said vertical incident wave and vertical reflection wave.

13. A focused ultrasonic inspection device according 12, wherein said through-hole is filled with a filler made of a material different in the propagating speed of an ultrasonic wave from a material which forms said acoustic lens.

14. A focused ultrasonic probe provided with a flat ultrasonic probe, an oscillator-setting surface of which is formed, as a planar surface, and an acoustic lens arranged on a free end portion of said flat ultrasonic probe and adapted to cause an ultrasonic wave, which has been transmitted from said oscillator, to converge, wherein said acoustic lens is provided, at a central part of an oscillator-facing side thereof, with an ultrasonic wave shielding member smaller than said oscillator arranged in said flat ultrasonic probe such that said ultrasonic probe is capable of performing propagation of an angled incident wave to a specimen and a leaked wave from said specimen but is incapable of performing propagation of a vertical incident wave to said specimen and a vertical reflection wave from said specimen.

15. A focused ultrasonic probe according to claim 11 or 14, wherein said acoustic lens is a cylindrical lens.

16. A focused ultrasonic probe according to claim 11 or 14, wherein said acoustic lens is detachably mounted on said free end portion of said flat ultrasonic probe.

17. A focused ultrasonic probe provided with a flat ultrasonic probe, an oscillator-setting surface of which is formed as a planar surface, and an acoustic lens arranged on a free end portion of said flat ultrasonic probe and adapted to cause ultrasonic waves, which have been transmitted from said oscillator, to converge, wherein said acoustic lens is constructed such that a propagation speed of a first one of said ultrasonic waves along propagation paths for a vertical incident wave to a specimen and a vertical reflection wave from said specimen and a propagation speed of a second one of said ultrasonic waves along propagation paths for an angled incident wave to said specimen and a leaked wave from said specimen differ from each other and that said propagation paths for said angled incident wave to said specimen and said leaked wave from said specimen are partly cut off.

18. A focused ultrasonic probe according to claim 17, wherein said acoustic lens is provided, at a central part of an oscillator-facing side thereof, with a through-hole which extends tov a lens curvature surface; and a slit narrower in width than a diameter of said through-hole is formed in said lens curvature surface.

19. A focused ultrasonic probe provided with a flat ultrasonic probe, an oscillator-setting surface of which is formed as a planar surface, and an acoustic lens arranged on a free end portion of said flat ultrasonic probe and adapted to cause an ultrasonic wave, which has been transmitted from an oscillator, to converge, wherein a recess is formed at a central part of a surface of said acoustic lens, said surface being located opposite said oscillator, a slit a width of which is narrower than a diameter of said recess is formed in a radial direction on said oscillator-opposing surface, and an ultrasonic-wave shielding material is filled or air is filled in a space formed by said recess and slit and a surface of said oscillator arranged on said flat ultrasonic wave probe such that propagation of a vertical incident wave to a specimen and a vertical reflection wave from said specimen is rendered impossible and propagation of an angled incident wave to said specimen and a leaked wave from said specimen is partly cut off.

20. An ultrasonic probe provided with a flat ultrasonic probe, an oscillator-setting surface of which is formed as a planar surface, and an acoustic lens arranged on a free end portion of said flat ultrasonic, wherein a slit is formed in an ultrasonic wave transmitting/receiving surface of said acoustic lens and an ultrasonic wave propagation path of said acoustic lens is partly cut off.

21. An ultrasonic probe according to claim 20, wherein said ultrasonic wave transmitting/receiving surface of said acoustic lens is formed as a concave lens curvature surface.

* * * * *